United States Patent [19]

Wiederkehr et al.

[11] 4,069,324
[45] Jan. 17, 1978

[54] SUBSTITUTED 7(α-AMINO PHENYLACETAMIDO)CEPHEM DERIVATIVES

[75] Inventors: René Wiederkehr, Pfeffingen; Hans Bickel, Binningen, both of Switzerland

[73] Assignee: Ciba-Geigy Corporation, Ardsley, N.Y.

[21] Appl. No.: 713,076

[22] Filed: Aug. 9, 1976

[30] Foreign Application Priority Data

Aug. 20, 1975 Switzerland .................. 10822/75

[51] Int. Cl.² .................. A61K 31/54; C07D 501/16
[52] U.S. Cl. .................. 424/246; 544/17
[58] Field of Search .................. 260/243 C; 424/246

[56] References Cited

U.S. PATENT DOCUMENTS

| 3,925,372 | 12/1975 | Chauvette | 260/243 C |
|---|---|---|---|
| 3,985,746 | 10/1976 | Koster et al. | 260/243 C |
| 3,994,887 | 11/1976 | Crooij et al. | 260/243 C |
| 3,998,819 | 12/1976 | DeMarinis | 260/243 C |
| 4,008,230 | 2/1977 | Koppel | 260/243 C |

OTHER PUBLICATIONS

Morrison et al., "Organic Chemistry" 1966, pp. 700–701.

*Primary Examiner*—Nicholas S. Rizzo
*Assistant Examiner*—David E. Wheeler
*Attorney, Agent, or Firm*—John J. Maitner

[57] ABSTRACT

The invention relates to 7β-[D-2-amino-2-(lower alkyl-sulphonylamino-phenyl)-acetylamino]-3-R-cephem-4-carboxylic acid, in which R denotes lower alkoxy or halogen with an atomic number of up to 35, and their salts, which compounds possess antibiotic properties.

6 Claims, No Drawings

SUBSTITUTED 7(α-AMINO PHENYLACETAMIDO)CEPHEM DERIVATIVES

The invention relates to 7β-[D-2-amino-2-(lower alkylsulphonylamino-phenyl)-acetylamino]-3-R-3-cephem-4-carboxylic acids (I), wherein R denotes lower alkoxy or halogen with an atomic number of up to 35, and their salts, processes for the manufacture of such compounds and also pharmaceutical formulations which contain these compounds as the active compound and to the use of these compounds, preferably in the form of pharmacological formulations.

Lower alkyl in lower alkylsulphonylamino preferably contains up to 4 carbon atoms and denotes, for example, ethyl, n-propyl, isopropyl, n-butyl or isobutyl and above all methyl. Lower alkylsulphonylamino can be in any position in the phenyl radical but above all is in the 3-position.

Lower alkoxy R preferably contains up to 4 carbon atoms and denotes, for example, ethoxy, n-propoxy, isopropoxy, n-butoxy or isobutoxy and, above all, methoxy, whilst halogen represents fluorine or bromine, but above all represents chlorine.

Salts are, in particular, non-toxic salts which can be used pharmaceutically, such as metal salts or ammonium salts, especially alkali metal salts and alkaline earth metal salts, for example sodium salts, potassium salts, magnesium salts or calcium salts, as well as ammonium salts with ammonia or suitable organic amines and compounds which can be used for forming the salts are, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylamino-ethyl ester, lower alkyleneamines, for example 1-ethylpiperidine, cycloalkylamines, for example bicyclohexylamine, or benzylamines, for example N,N'-dibenzyl-ethylenediamine, and also bases of the pyridine type, for example pyridine, collidine or quinoline. The new compounds can also form acid addition salts, for example with inorganic acids, such as hydrochloric acid, sulphuric acid or phosphoric acid, or with suitable organic carboxylic or sulphonic acids, for example trifluoroacetic acid or 4-methylphenylsulphonic acid. The new compounds are preferably in the form of their inner salts, that is to say in the zwitterionic form.

The new compounds of the present invention display valuable pharmacological properties. Thus, in the free form or in the form of their salts they are active in vitro in a dosage range of 0.05 to 100 mcg/ml against cocci, such as *Staphylococcus aureus, Streptococcus pyogenes, Streptococcus haemolyticus, Streptococcus faecalis, Diplococcus pneumoniae, Neisseria gonorrhoeae* and *Neisseria meningitidis*, in a dosage range of 0.8 to 50 mcg/ml against enterobacteria, such as *Escherichia coli, Salmonella species, Shigella flexneri, Klebsiella pneumoniae, Proteus vulgaris, Proteus rettgeri* and *Proteus mirabilis* and in a dosage range of 0.4 to 12.5 mcg/ml against other pathogenic germs, such as *Haemophilus influenzae* and *Pasteurella multocida*. On parenteral or, in particular, oral administration, they are active against microorganisms, such as Gram-positive bacteria, for example *Staphylococcus aureus, Streptococcus pyogenes* and *Diplococcus pneumoniae* (for example in mice in doses of about 0.5 to about 100 mg/kg, given subcutaneously or perorally) and Gram-negative bacteria, for example *Escherichia coli, Salmonella typhimurium, Shigella flexneri, Klebsiella pneumoniae, Proteus vulgaris, Proteus rettgeri* and *Proteus mirabilis* (for example in mice in does of about 3.0 to about 200 mg/kg, given subcutaneously or perorally) and especially also against penicillin-resistant bacteria, and are of low toxicity.

Compared with the 3-substituted 3-phenylglycylamino-3-cephem-4-carboxylic acids which are known from German Offenlegungsschriften Nos. 2,331,133 and 2,408,698 and which do not contain a lower alkylsulphonylamino group in the phenyl nucleus, the compounds of the present invention are distinguished by a higher in vitro activity against many of the strains of enterobacteria. In vivo, in mice, they are distinctly superior to these known formulations, both against many infections by cocci and against infections by enterobacteria. Compared with the 3-substituted 7β-[2-(lower alkylsulphonylaminophenyl)-glycylamino]-3-cephem-4-carboxylic acids which are known from German Offenlegungsschriften Nos. 2,422,385 and 2,432,190, the new compounds are distinguished by an increased in vitro and in vivo (mice) activity, especially against strains of enterobacteria. Moreover, they are highly soluble in water and urine and this makes the possibility of crystalluria appear slight. The new compounds can be used, for example in the form of formulations having an antibiotic action, for the treatment of the infections mentioned.

The invention relates above all to 7β-[D-2-amino-2-(3-methylsulphonylamino-phenyl)-acetylamino]-3-R'-3-cephem-4-carboxylic acids, wherein R' represents methoxy or chlorine, and their salts, especially their non-toxic salts which can be used pharmaceutically and in particular their inner salts.

The new compounds are manufactured in a manner which is in itself known. Thus, for example, they can be obtained when the hydroxyl group in a 7β-[D-2-amino-2-(lower alkylsulphonylamino-phenyl)-acetylamino]-3-hydroxy-3-cephem-4-carboxylic acid (II), wherein the carboxyl group is in a protected form, the 2-amino group is preferably in a protected form and the lower alkylsulphonylamino group is optionally in a N-acylated form, is converted into the radical R and, if necessary, in a resulting compound a protected 2-amino group and/or a N-acylated lower alkylsulphonylamino group are converted into the free amino group and into the lower alkylsulphonylamino group respectively, and/or the protected carboxyl group is converted into a free carboxyl group, and, if desired, a resulting salt is converted into the free compound or into another salt, and/or a free compound is converted into a salt.

In the above starting material, the carboxyl group is in a protected form and the amino group is usually in a protected form and possible protective groups are, in particular, the radicals used in penicillin and cephalosporin chemistry and in peptide chemistry.

The carboxyl group is usually protected in an esterified form and an ester grouping of this type can be split easily under mild conditions. Possible groups which are suitable as protected carboxyl groups are, in particular, lower alkoxycarbonyl, especially tert.-lower alkoxycarbonyl, for example tert.-butoxycarbonyl, polycycloalkoxycarbonyl, for example adamantyloxycarbonyl, arylmethoxycarbonyl, wherein aryl preferably represents one or two phenyl radicals, which are optionally monosubstituted or polysubstituted, for example by lower alkyl, especially tert.-lower alkyl, for example tert.-butyl, lower alkoxy, such as methoxy, hydroxyl, halogen, for example chlorine, and/or nitro, such as benzyloxycarbonyl which is optionally substituted, for example as mentioned above, for example 4-nitro-benzyloxycarbonyl, or diphenylmethoxycarbonyl which is substituted, for example as mentioned above, for example benzhydryloxycarbonyl or di-(4-methoxyphenyl)-methoxycarbonyl, or 2-halogeno-lower alkoxycarbonyl, for example 2,2,2-trichloroethoxycarbonyl or 2-bromo- or 2-iodo-ethoxycarbonyl, or acylmethoxycarbonyl, especially aroylmethoxycarbonyl, wherein the aroyl group preferably represents benzoyl which is optionally substituted, for example by halogen, such as bromine, for example phenacyloxycarbonyl. Esterified carboxyl groups are also corresponding silyloxycarbonyl groups, especially organic silyloxycarbonyl groups. In these groups, the silicon atom preferably has lower alkyl, especially methyl, and also lower alkoxy, for example methoxy, and/or halogen, for example chlorine, as substituents. Suitable silyl protective groups are, above all, tri-lower alkylsilyl, especially trimethylsilyl, and also dimethyl-tert.-butylsilyl, lower alkoxy-lower alkyl-halogeno-silyl, for example methoxymethyl-chloro-silyl, or di-lower alkyl-halogeno-silyl, for example dimethyl-chloro-silyl. Silyl protective groups, especially those which contain a halogen atom as a substituent, can at the same time protect the carboxyl groups in two different molecules of the starting material; that is to say in groups of this type such a halogen atom has been replaced by the carbonyl group of a further molecule of the starting material.

A preferred protected carboxyl group is, in particular, benzyloxycarbonyl which is optionally substituted, for example as mentioned, for example 4-nitrobenzyloxycarbonyl, or diphenylmethoxycarbonyl which is optionally substituted, for example as mentioned, for example benzhydryloxycarbonyl.

A protected 2-amino group can be, for example, in the form of an acylamino, triarylmethylamino, etherified mercaptoamino, 1-acyl-2-lower alkylideneamino or silylamino group, which can be split easily, or in the form of an azido group.

In a corresponding acylamino group, and in a N-acyl-lower alkylsulphonylamino group, acyl is preferably the acyl radical of a carbonic acid half-ester, such as lower alkoxycarbonyl, especially tert.-lower alkoxycarbonyl, for example tert.-butoxycarbonyl, polycycloalkoxycarbonyl, for example adamantyloxycarbonyl, arylmethoxycarbonyl, wherein aryl preferably represents one or two phenyl radicals which are optionally monosubstituted or polysubstituted, for example by lower alkyl, especially tert.-lower alkyl, for example tert.-butyl, lower alkoxy, such as methoxy, hydroxyl, halogen, for example chlorine, and/or nitro, such as benzyloxycarbonyl which is optionally substituted, for example as mentioned above, for example b 4-nitro-benzyloxycarbonyl, or diphenylmethoxycarbonyl which is substituted, for example as mentioned above, for example benzhydryloxycarbonyl or di-(4-methoxyphenyl)-methoxycarbonyl, or 2-halogeno-lower alkoxycarbonyl, for example 2,2,2-trichloroethoxycarbonyl, 2-bromoethoxycarbonyl or 2-iodoethoxycarbonyl, or acylmethoxycarbonyl, especially aroylmethoxycarbonyl, wherein the aroyl group preferably represents benzoyl which is optionally substituted, for example by halogen, such as bromine, for example phenacyloxycarbonyl. Acyl in an acylamino group or in a N-acyl-lower alkylsulphonylamino group can also represent the corresponding radical of an organic sulphonic acid; such a radical is, in particular, arylsulphonyl, wherein aryl denotes a phenyl radical which is optionally substituted, for example by lower alkyl, such as methyl, halogen, such as bromine, or nitro, for example 4-methylphenylsulphonyl.

In a triarylmethylamino group, the aryl radicals are, in particular, optionally substituted phenyl radicals; a corresponding group is, above all, trityl.

An etherified mercapto group in an amino group protected by such a radical is, above all, arylthio or aryllower alkylthio, wherein aryl is, in particular, phenyl which is optionally substituted, for example by lower alkyl, such as methyl or tert.-butyl, lower alkoxy, such as methoxy, halogen, such as chlorine, and/or nitro. A corresponding amino protective group is, for example, 4-nitrophenylthio.

In a 1-acyl-2-lower alkylidene radical which can be used as an amino protective group, acyl is preferably the corresponding radical of a lower alkanecarboxylic acid, of a benzoic acid which is optionally substituted, for example by lower alkyl, such as methyl or tert.-butyl, lower alkoxy, such as methoxy, halogen, such as chlorine, and/or nitro, or of a carbonic acid half-ester, such as of a carbonic acid lower alkyl half-ester. Corresponding protective groups are, above all, 1-lower alkanoyl-2-propylidene, for example 1-acetyl-2-propylidene, or 1-lower alkoxycarbonyl-2-propylidene, for example 1-ethoxycarbonyl-2-propylidene.

A silylamino group is, above all, an organic silylamino group wherein the silicon atom preferably has lower alkyl, especially methyl, and also lower alkoxy, for example methoxy, and/or halogen, for example chlorine, as substituents. Corresponding silyl groups, are, above all, tri-lower alkylsilyl, especially trimethylsilyl, and also dimethyl-tert.-butyl-silyl, lower alkoxy-lower alkyl-halogeno-silyl, for example methoxy-methyl-chloro-silyl, or di-lower alkylhalogeno-silyl, for example dimethyl-chloro-silyl. Silyl protective groups, especially those which contain a halogen atom as a substituent, can at the same time protect the amino group in two different molecules of the starting material; that is to say in groups of this type the halogen atom has been replaced by the amino group of a further molecule of the starting material.

The 2-amino group in the starting material II can also be protected in a protonised form; possible anions are, above all, those of strong inorganic acids, such as of hydrogen halide acids, for example the chlorine or bromine anion.

Preferred amino protective groups are the acyl radicals of carbonic acid half-esters, especially tert.-lower alkoxycarbonyl, or benzyloxycarbonyl or diphenylmethoxycarbonyl, which are optionally substituted, for example as indicated, or 2-halogeno-lower alkoxycarbonyl.

The starting material II is preferably in the indicated 3-hydroxy-3-cephem form but can also be employed in the corresponding tautomeric cepham-3-one form.

The conversion of the hydroxyl group in a starting material of the formula II into lower alkoxy R can be effected by etherification with a lower alkyl radical in a manner which is in itself known. Thus, the starting material can be reacted, for example, with a diazo-lower alkane, for example diazomethane, diazoethane or diazo-n-butane. Such a reagent is used in the presence of a suitable inert solvent, such as an aliphatic or aromatic hydrocarbon which is optionally substituted, for example which contains halogen, such as chlorine, or of a solvent mixture and, depending on the diazo reagent, with cooling, at room temperature or with slight warming, and also, if necessary, in a closed vessel and/or under an inert gas atmosphere, for example a nitrogen atmosphere. It can optionally also be manufactured in situ.

Furthermore, a starting material II can be converted into a compound I, wherein R represents lower alkoxy, by treatment with a reactive ester of a lower alkanol. Suitable esters are, above all, those with strong inorganic or organic acids, such as mineral acids, for example hydrogen halide acids, such as hydrochloric acid, hydrobromic acid or hydriodic acid, and also sulphuric acid or strong organic sulphonic acids, such as lower alkanesulphonic acids which are optionally substituted, for example by halogen, such as fluorine, or halogenosulphonic acids or aromatic sulphonic acids, such as, for example, benzenesulphonic acids which are optionally substituted, for example by lower alkyl, such as methyl, halogen, such as bromine, and/or nitro, for example methanesulphonic acid, fluorosulphonic acid, trifluoromethanesulphonic acid or p-toluenesulphonic acid. These reagents, and especially di-lower alkyl sulphates, such as dimethyl sulphate, or optionally halogen-substituted methanesulphonic acid lower alkyl esters, for example methyl trifluoromethanesulphonate, and halogenosulphonic acid lower alkyl esters, for example methyl fluorosulphonate, are customarily used in the presence of a solvent, such as an aliphatic, cycloaliphatic or aromatic hydrocarbon which is optionally substituted, for example by halogen, such as chlorine, for example methylene chloride, an ether, such as dioxane or tetrahydrofurane, or a lower alkanol, such as methanol, or of a solvent mixture. For such reactions, suitable condensing agents, such as alkali metal carbonates or bicarbonates, for example sodium carbonate or bicarbonate or potassium carbonate or bicarbonate (usually together with a sulphate), or organic bases, such as tri-lower alkylamines, preferably sterically hindered tri-lower alkylamines, for example N,N-di-isopropyl-N-ethylamine (usually together with lower alkyl halogenosulphates or optionally halogen-substituted methanesulphonic acid lower alkyl esters) are preferably used and the reaction is carried out with cooling, at room temperature or with warming, for example at temperatures of about −20° C to about 50° C and, if necessary, in a closed vessel and/or in an inert gas atmosphere, for example a nitrogen atmosphere.

The conversion of a starting material II into a compound I, wherein R represents lower alkoxy, can also be carried out by treatment with a compound which contains two or three lower alkoxy groups on the same carbon atom of aliphatic character, that is to say with a corresponding acetal or ortho-ester, in the presence of an acid agent. Thus, for example, gem-lower alkoxy-lower alkanes, such as 2,2-dimethoxypropane, can be used as etherifying agents, in the presence of a strong organic sulphonic acid, such as p-toluenesulphonic acid, and of a suitable solvent, such as a lower alkanol, for example methanol, or a di-lower alkyl sulphoxide or lower alkylene sulphoxide, for example dimethylsulphoxide, or orthoformic acid tri-lower alkyl esters, for example triethyl orthoformate, can be used as etherifying agents, in the presence of a strong acid, such as a mineral acid, for example sulphuric acid, or a strong organic sulphonic acid, such as p-toluenesulphonic acid, and of a suitable solvent, such as a lower alkanol, for example ethanol, or an ether, for example dioxane.

Compounds I, wherein R denotes lower alkoxy, can also be obtained when starting materials II are reacted with tri-lower alkyl-oxonium salts, and also di-lower alkoxycarbenium salts or di-lower alkylhalonium salts, wherein halonium is, in particular, bromonium, and in particular corresponding salts with complex, fluorine-containing acids, such as the corresponding tetrafluoborates, hexafluorophosphates or hexafluoroantimonates, or hexachloroantimonates. Such reagents are, for example, trimethyloxonium hexafluoroantimonate, hexachloroantimonate, hexafluorophosphate or tetrafluoroborate or triethyloxonium hexafluoroantimonate, hexachloroantimonate, hexafluorophosphate or tetrafluoborate, dimethoxycarbenium hexafluorophosphate or dimethylbromonium hexafluoroantimonate. These etherifying agents are preferably used in an inert solvent, such as an ether or a halogenated hydrocarbon, for example diethyl ether, tetrahydrofurane or methylene chloride, or in a mixture thereof, if necessary in the presence of a base, such as an organic base, for example a tri-lower alkylamine, preferably a sterically hindered tri-lower alkylamine, for example N,N-diisopropyl-N-ethylamine, and with cooling, at room temperature or with slight warming, for example at about −20° C to about 50° C, if necessary in a closed vessel and/or in an inert gas atmosphere, for example a nitrogen atmosphere.

Etherification of the enol hydroxyl group in a starting material II can also be produced by treatment with a 1-lower alkyl-triazene compound substituted in the 3-position, in which the substituent on the nitrogen atom in the 3-position denotes an organic radical bonded via a carbon atom, preferably a carbocyclic aryl radical, such as an optionally substituted phenyl radical, for example lower alkylphenyl, such as 4-methyl-phenyl. Triazene compounds of this type are 3-aryl-1-lower alkyl-triazenes, for example 3-(4-methylphenyl)-1-methyl-triazene. These reagents are customarily used in the presence of inert solvents, such as optionally halogenated hydrocarbons or ethers, for example benzene, or solvent mixtures, and with cooling, at room temperature and, preferably, at elevated temperature, for example at about 20° C to about 100° C, if necessary in a closed vessel and/or in an inert gas atmosphere, for example a nitrogen atmosphere.

Replacement of the hydroxyl group in a starting material II by halogen can be carried out in diverse ways, usually by treatment with a halogenating agent, that is to say a fluorinating, chlorinating or brominating agent.

Compounds I, wherein Hal denotes fluorine, chlorine or bromine, can be manufactured, for example, by treating a starting material II with a phosphorus reagent whic replaces enol hydroxyl groups by halogen, and subsequently splitting off the protective groups which are present.

Examples of phosphorus reagents of this type are dihalogeno-triorganyl-phosphoranes, trihalogeno-diorganylphosphoranes or a mixture consisting of a triorganyl-phosphine and a carbon tetrahalide.

In these reagents halogen is fluorine, chlorine or bromine. In the carbon tetrahalide, halogen is preferably chlorine or bromine. The organyl radicals in the phosphoranes and phosphines represent organic radicals with up to 18 carbon atoms and can be identical or different.

Organyl radicals are, in particular, hydrocarbon radicals which have up to 18, in particular up to 12 and preferably up to 6, carbon atoms and are optionally substituted, for example by tertiary amino groups, or bonded to polymers, such as lower alkyl radicals, for example methyl, ethyl or propyl, di-lower alkylamino-lower alkyl radicals, for example 3-dimethylaminopropyl, carbocyclic radicals, such as phenyl which is optionally substituted as indicated, and also phenyl substituted by polymers, for example by polystyrene crosslinked with divinylbenzene, or phenyl substituted by di-lower alkylamino-lower alkyl, for example dimethylaminomethyl. In the case of phenyl substituted by polymers there is usually only one radical present on a given phosphorus atom.

Further organic radicals are secondary amino radicals, such as di-lower alkylamino, above all dimethylamino.

Representative examples of the said phorphoranes are dihalogeno-triphenyl-phosphoranes or trihalogeno-diphenylphosphoranes, such as difluoro-triphenyl-, trifluorodiphenyl-, dichloro-triphenyl-, trichloro-diphenyl-, dibromo-triphenyl- and tribromo-diphenyl-phosphorane, wherein one of the phenyl groups can be linked to a polymer, such as a polystyrene crosslinked with divinylbenzene, or can be substituted by dimethylaminomethyl.

Representative examples of the said phosphines are triethyl-, methyl-propyl-phenyl-, bis-(3-dimethylaminopropyl)-phenyl-, tris-(dimethylamino)-, bis-(dimethylamino)-phenyl-and especially triphenyl-phosphine, wherein one of the phenyl groups can be linked to a polymer, such as a polystyrene crosslinked with divinylbenzene.

Examples of carbon tetrahalides are carbon tetrabromide and especially carbon tetrachloride.

The reaction with the halogenating phosphorus reagents takes place in a manner which is in itself known in an inert, aprotic, preferably polar solvent, such as a chlorinated hydrocarbon, for example methylene chloride, chloroform, carbon tetrachloride or 1,2-dichloroethane, a nitrile, such as acetonitrile or benzonitrile, or a N,N-disubstituted carboxylic acid amide, such as dimethylformamide or N,N-dimethylacetamide, or mixtures thereof, and, depending on the reactivity of the reagent employed, with cooling or warming, that is to say at temperatures between about $-60°$ C and the reflux temperature of the solvent used, and optionally in an inert gas atmosphere, such as a nitrogen atmosphere. When tri-lower alkyl-phosphines or tris-(di-lower alkylamine)-phosphines and carbon tetrachloride or carbon tetrabromide are used, cooling to about $-60°$ to $-20°$ C is generally necessary.

The halogenating phosphoranes mentioned can also be formed in situ, for example by reacting the said phosphines with the desired carbon tetrahalide, in which case other halogenating phosphorus compounds can also be formed in addition to the dihalogeno-triorganyl phosphorane, or by treating the phosphines with halogen, for example chlorine, or by reacting triorganyl-phosphine oxides with a dihalogenocarbonyl, such as phosgene, or trihalogeno-silane, such as trichlorosilane.

When the halogenation reaction is carried out with the said phosphoranes, a weak base, such as pyridine or a N,N-di-lower alkylaniline, such as N,N-dimethylaniline, can be added to the reaction medium in order to take up the hydrogen halide formed.

In a preferred embodiment, a starting material II, in one of the inert aprotic solvents mentioned, such as methylene chloride, is treated, at room temperature, that is to say about 20° – 25° C, with the carbon tetrahalide, preferably in excess, and then with the triphenylphosphine, in amounts of about 1.2 to 2 equivalents of the starting material, and the reaction mixture is left to stand, or stirred, at the same temperature until the halogenation is complete.

Compounds I, wherein Hal denotes chlorine or bromine, can be obtained, for example, by treating the starting material II with a corresponding N,N-disubstituted halogenoiminium halide compound, especially of the formula

(III)

In the formula III, $R_1$ and $R_2$ represent organic radicals, for example aliphatic radicals, above all lower alkyl and especially methyl, and $R_3$ in particular represents hydrogen but can also be an organic radical, for example an aliphatic radical, such as lower alkyl, especially methyl, whilst Hal is chlorine or bromine.

The above reagent is usually manufactured in situ by treating a suitable N,N-disubstituted amide of the formula

(IV)

wherein $R_1$, $R_2$ and $R_3$ have the abovementioned meanings, in particular a corresponding N,N-disubstituted formamide and above all dimethylformamide, with one of the chlorinating or brominating agents customarily used. The latter are suitable carbonic acid halides, for example phosgene or carbonyl dibromide, carboxylic acid halides, for example oxalyl chloride or oxalyl bromide, sulphuric acid halides, for example thionyl chloride or thionyl bromide, or phosphoric acid chlorides, for example phosphorus trichloride, phosphorus oxychloride, phosphorus tribromide or phosphorus oxybromide, and also phosphorus pentachloride. Particularly preferred chlorinating and brominating agents are phosphorus trichloride and phosphorus tribromide.

The above reaction is usually carried out in the presence of a solvent or diluent and an amide of the formula IV which is also suitable as a solvent, in particular dimethylformamide, which preferably is in the anhydrous form, can customarily be used as such a solvent or diluent. In addition to the amide, which customarily is dimethylformamide, and also dimethylacetamide, and is usually present in excess, and thus also serves as the solvent, it is also possible correspondingly to use ether-like solvents, for example tetrahydrofurane or dioxane, halogenated hydrocarbons, for example methylene chloride, or sulphoxides, for example dimethylsulphoxide.

The above chlorinating and brominating agents are customarily used in amounts which correspond to two equivalents of the 3-hydroxy-3cephem starting material II. The reaction can, for example, be carried out by adding the chlorinating or brominating agent to a solution of the 3-hydroxy-3-cephem starting material II in the amide of the formula IV, especially in dimethylformamide. In this case this solution is kept at a temperature of about 0° C to about 15° C, after which the reaction mixture is left to stand for several hours at room temperature. The reaction is initially exothermic; the reaction vessel therefore has to be so cooled that the temperature can be kept below about 25° C during this reaction phase. The reaction mixture is then left to stand at about room temperature for the remainder of the reaction period and the course of the reaction can be followed by thin layer chromatography.

The chlorination or bromination can also be carried out by first mixing the chlorinating or brominating agent with the amide of the formula IV, especially dimethylformamide, and thus forming the halogenoiminium halide of the formula III and then reacting the latter with a solution of the 3-hydroxy-3-cephem starting material II in the amide, especially in dimethylformamide, to which an additional solvent can also be added, or in another solvent, for example tetrahydrofurane.

If necessary, the reaction is carried out in an inert gas atmosphere.

The conversion of the 3-hydroxyl group into fluorine can be effected, for example, by treating the starting material II with a reagent of the formula $F_3S—Am$, wherein Am represents a disubstituted amino group; such reagents have been described, inter alia, by Markovsky et al., Synthesis, Volume 1973, page 787. The amino group contains as substituents preferably two monovalent hydrocarbon radicals which are optionally substituted and above all aliphatic or also aromatic, or one divalent, optionally substituted hydrocarbon radical which is preferably aliphatic. Monovalent aliphatic hydrocarbon radicals are, above all, lower alkyl, for example methyl, ethyl, n-propyl, isopropyl or straight-chain or branched butyl, whilst a corresponding aromatic hydrocarbon radical is preferably phenyl which is optionally substituted, for example by lower alkyl, such as methyl, lower alkoxy, such as methoxy, and/or halogen, for example chlorine. In a divalent aliphatic hydrocarbon radical, carbon atoms can optionally be replaced by hetero-atoms, such as an oxygen atom or an optionally substituted nitrogen atom; divalent radicals of this type are lower alkylene, for example 1,4-butylene or 1,5-pentylene, oxa-lower alkylene, for example 3-oxa-1,5-pentylene, or optionally N-lower alkyl-substituted aza-lower alkylene, for example 3-methyl-3-aza-1,5-pentylene. The group Am therefore above all represents di-lower alkylamino, for example dimethylamino, diethylamino, ethyl-methyl-amino, methyl-propyl-amino, di-n-propyl amino or diisopropylamino, lower alkyl-phenyl-amino, for example methyl-phenyl-amino or ethyl-phenyl-amino, lower alkyleneamino, for example pyrrolidino or piperidino, oxa-lower alkyleneamino, for example morpholino, or optionally aza-lower alkyl-substituted aza-lower alkyleneamino, for example 4-methyl-piperazino.

The above reaction is preferably carried out in the presence of a suitable inert solution, in which case, for example, optionally substituted carbocyclic hydrocarbons, for example alicyclic hydrocarbons, such as cyclopentane, cyclohexane, cycloheptane or decahydronaphthalene, or aromatic carbocyclic hydrocarbons, such as benzene, toluene, toluene or xylenes, which can also be halogenated in the nucleus, such as chlorobenzene, dichlorobenzenes or bromobenzene, and in particular saturated aliphatic hydrocarbons, such as pentanes, hexanes, heptanes and octanes, or corresponding halogenated, and in particular chlorinated, hydrocarbons, such as chloroform, 1,1- or 1,2-dichloroethane, 1,1-, 1,2- or 1,3-dichloropropane and above all methylene chloride, are used. Further solvents which can also be used are aliphatic and, in particular, cyclic ethers, such as diethyl ether, diisopropyl ether, ethylene glycol dimethyl ether, tetrahydrofurane and, above all, dioxane, as well as nitrogen-containing aromatic heterocyclic compounds, such as pyridine and its homologues or quinoline. Optionally, an excess of the fluorinating agent can be used as the solvent and/or several of the said solvents can be combined with one another. If necessary, the reaction is carried out wih cooling or warming, for example in a temperature range of about −20° C to about 80° C, and preferably of about 0° C to about 30° C, and/or under an inert gas atmosphere.

A fluorine atom can also be introduced when a starting material II in which the hydroxy group is in the form of an organic sulphonyloxy group, that is to say a 7β-[D-2-amino-2-(lower alkylsulphonylamino-phenyl)-acetylamino]-3-sulphonyloxy-3-cephem-4-carboxylic acid (IIa), wherein the carboxyl group is in a protected form and the amino group is preferably in a protected form and the sulphonyloxy group represents an organic sulphonyloxy group, is reacted with an inorganic fluoride in the presence of a crown ether and, if necessary and desired, the additional process steps are carried out.

An organic sulphonyloxy group is, above all, lower alkylsulphonyloxy, especially methylsulphonyloxy, but can also be arylsulphonyloxy, wherein aryl is preferably phenyl which is optionally substituted, for example by lower alkyl, such as methyl, halogen, for example bromine, or nitro, for example 4-methyl-phenylsulphonyloxy.

An inorganic fluoride is, above all, a metal fluoride and, in particular, an alkali metal fluoride, for example sodium fluoride, or a heavy metal fluoride, for example silver fluoride, is used.

The coronene ethers which are used conjointly with the inorganic fluoride are optionally substituted 18-coronene-6-ethers, such as dicyclohexyl-18-coronene-6-ether.

The reaction is carried out in the presence of an inert solution, especially a nitrile, for example acetonitrile or propionitrile, or a nitro-lower alkane, for example nitromethane or nitroethane, under essentially anhydrous conditions and, if necessary, with cooling, for example in a temperature range of about −20° C to about 25° C, and preferably at about room temperature, and/or in an inert gas atmosphere.

The 3-sulphonyloxy-3-cephem starting material (IIa) can also be formed in situ, since any 7β-[D-2-amino-2-(lower alkylsulphonylamino-phenyl)-acetylamino]-3-sulphonyloxy-2-cephem-4ξ-carboxylic acid (IIb) which may be present together with the starting material IIa and wherein the carboxyl group is in a protected form and the amino group is preferably in a protected form and the sulphonyloxy group represents an organic sulphonyloxy group, is converted, under the reaction conditions, into the corresponding 3-sulphonyloxy-3-cephem starting material IIa and enters as such into the reaction with the fluorinating agent.

The starting material II can be manufactured, for example, by acylating the amino group in a 7β-amino-3-hydroxy-3-cephem-4-carboxylic acid (V), wherein the carboxyl group and the 3-hydroxyl group are in a protected form and the carboxyl group is in particular in an esterified form and the 3-hydroxyl group is in particular in a silylated form, with a D-2-amino-2-(lower alkylsulphonylamino-phenyl)-acetyl radical. The acylation can be carried out, for example, by the methods described below and the 2-amino group in the acylating agent is preferably in a protected form and the lower alkylsulphonylamino group is optionally in a N-acylated form. The hydroxyl group of the enol grouping can be converted into a sulphonyloxy group, for example by treatment with an organic sulphonic acid halide, for example an organic sulphonic acid chloride, in the presence of a tertiary amine, such as triethylamine, or of dimethylformamide and propylene oxide.

The new compounds can also be obtained when the 7β-amino group in a 7β-amino-3-R-3-cephem-4-carboxylic acid (VI), wherein the carboxyl group is optionally in a protected form and the 7β-amino group is optionally in a reactive protected form, that is to say in a form which permits acylation, is acylated with a D-2-amino-2-(lower alkylsulphonylamino-phenyl)-acetyl radical and, if necessary or desired, the additional measures are carried out.

In a starting material VI, the carboxyl group can preferably be protected in an esterified form, for example as described above and above all in the form of a silyl ester, such as a trimethylsilyl ester (which usually is prepared immediately prior to the acylation reaction by treatment with a corresponding silylating agent, for example trimethyl-chlorosilane or bis-(trimethylsilyl)-acetamide). However the carboxylic acid starting material VI can also be employed in the form of a salt, for example in the form of an ammonium salt, such as in the form of a triethylammonium salt, or in a protected form, which is obtainable by reacting the carboxylic acid starting material VI with a suitable organic phosphorus halide compound, such as with a lower alkyl- or lower alkoxy-phosphorus dihalide, such as methyl-phosphorus dichloride, ethyl-phosphorus dibromide or methoxy-phosphorus dichloride. A 7β-amino group in a reactive protected form is, for example, a 7β-amino group protected by a silyl radical, such as one of the corresponding radicals mentioned above.

Further groups which can protect the 7β-amino group in a reactive form are the carbonyl group (O=C=), and also 1-halogeno- or 1-alkoxy-methylene groups, which are optionally substituted in the 1-position. In such methylene groups, halogen is bromine or, in particular, chlorine and alkoxy is, in particular, optionally substituted lower alkoxy, such as ethoxy, propoxy, butoxy or preferably, methoxy. The other substituent in the 1-position of such a methylene group is hydrogen or any organic radical which has less steric hindrance, for example optionally substituted lower alkyl, such as methyl, 4-amino-4-caboxybutyl, wherein the amino group and the carboxyl group can be protected, benzyl, phenoxymethyl and thienylmethyl or also furylmethyl, such as 2-thienylmethyl or 2-furylmethyl.

The acylation of the free 7β-amino group, or of the reactive protected 7β-amino group, in the starting material VI is carried out in a manner which is in itself known. Acylating agents which can be used are a D-2-amino-2-(lower alkylsulphonylamino-phenyl)-acetic acid (VII) or a reactive derivative thereof and the 2-amino group can usually be present in a protected form, inter alia also in a protonised or masked form, for example also as an azido group, and the lower alkylsulphonylamino group can optionally be substituted on the nitrogen by an acyl group.

If the free acid VII having a protected 2-amino group and an optionally N-acylated lower alkylsulphonylamino group is employed for the acylation, suitable condensing agents, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium 3'-sulphonate and N-tert.-butyl-5-methyl-isoxazolinium perchlorate, or a suitable acylamino compound, for example 2-ethoxy-1-ethoxycarbonyl-1,2-dihydroquinoline are customarily used. The condensation reaction is preferably carried out in an anhydrous reaction medium, for example in methylene chloride, dimethylformamide or acetonitrile.

Further suitable condensing agents for the acylation of the 7β-amino group by a D-2-amino-2-(lower alkylsulphonylamino-phenyl)-acetic acid, which can also be used in the form of its esters, for example the lower alkyl esters, such as the methyl or ethyl ester, and wherein the 2-amino group can be in a protected form and the lower alkylsulphonylamino group can be in a N-acylated form, are the enzymes, which catalyse the acylation, of suitable micro-organisms, for example of Pseudomonas melanogenum ATCC 17,808, or of numerous other known acylating strains, such as Xanthomonas, Acetobacter, Achromobacter, *Beneckea hyperoptica*, *Micrococcus urea*, *Mycobacterium smegmatis* or *Norcardia globerula*. The enzymatic acylation is carried out in a manner which is in itself known, in the presence of the said micro-organisms, either in an aqueous nutrient medium which contains the known nutrients necessary for growth of the strain used, or in a buffer solution, for example an acetate buffer containing sodium chloride, under aerobic conditions at temperatures between about 20° and about 50°, and at a pH value of 5 to 9, and preferably 6.5 to 7.

A reactive derivative of the said acid VII, which usually has a protected amino group and an optionally N-acylated lower alkylsulphonylamino group, is, above all, an anhydride thereof, including, and preferably, a mixed anhydride. Mixed anhydrides are, for example, those with inorganic acids, especially with hydrogen halide acids, that is to say the corresponding acid halides, for example the acid chloride or acid bromide, and also the anhydride with hydrazoic acid, that is to say the corresponding acid azide, or with a phosphorus-containing acid, for example phosphoric acid or phosphorous acid, with a sulphur containing acid, for example sulphuric acid, or with a halide, such as the chloride, of the dimethylimmoniomethyl half-ester of sulphurous acid, or with hydrocyanic acid. Other mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl or isobutyl half-ester, or with a halide, such as the chloride, of the N,N-dimethylimmoniomethyl half-ester of carbonic acid, or with organic, and especially aliphatic or aromatic, sulphonic acids, for example p-toluenesulphonic acid.

Further acid derivatives which are suitable for reaction with the amino group in the starting material VI are activated esters of the said acid VII, which usually have a protected amino group, such as esters with vinylogous alcohols (that is to say enols), such as vinylogous lower alkenols, or aryl esters, such as phenyl esters which are preferably substituted, for example by nitro or halogen, such as chlorine, for example pentachlorophenyl, 4-nitrophenyl or 2,4-dinitrophenyl esters, hetero-aromatic esters, such as benztriazole esters, or diacylamino-esters, such as succinylimino- or phthalylimino-esters.

The acylation with an acid derivative, such as an anhydride, and especially with an acid halide, can be carried out in the presence of an acid-binding agent, for example an organic base, such as an organic amine, for example a tertiary amine, such as a tri-lower alkylamine, for example triethylamine, a N,N-di-lower alkyl-aniline, for example N,N-dimethylaniline, or a base of the pyridine type, for example pyridine, or an inorganic base, for example an alkali metal hydroxide, carbonate or bicarbonate or alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or 1,2-propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at a lowered or elevated temperature, for example at about 20° to about +100° C, and/or in an inert gas atmosphere, for example a nitrogen atmosphere.

If the 7β-amino group in the starting material VI has been protected by a radical which permits acylation, this radical is split off during the acylation, or when the reaction product is worked up, for example by hydrolysis, optionally in the presence of a base, such as triethylamine.

The starting materials VI are known and can be manufactured, for example, by splitting the acylamino grouping in 7β-acylamino-3-R-3-cephem-4-carboxylic acid compounds wherein acyl denotes a radical which differs from a D-2-amino-2-(lower alkylsulphonylamino-phenyl)-acetyl radical, for example phenylacetyl or phenoxyacetyl, in a manner which is in itself known, for example by treatment with phosphorus pentachloride in the presence of pyridine, followed by methanol and, if desired, water.

Starting materials VI in which the 7β-amino group is protected in a reactive form which permits acylation are also known or can be manufactured analogously to known methods, optionally in situ. A silyl group is introduced by treating the free 7β-amino group with a corresponding silylating agent, for example trimethylchlorosilane or bis-(trimethylsilyl)-acetamide. A carbonyl group can be introduced by treating the free 7β-amino group with phosgene in the presence by treating the free 7β-amino group with the phosgene in the presence of a base, such as a tertiary amine, for example triethylamine. Starting materials VI in which the amino group is protected by a 1-halogenomethylene group which is optionally substituted in the 1-position are obtained by treating a 7β-acylamino-3-R-3-cephem-4-carboxylic acid (IX), wherein acyl represents an acyl radical which differs from a D-2-amino-2-(lower alkylsulphonylaminophenyl)-acetyl (in which amino is optionally protected), for example an optionally substituted lower alkanoyl radical, such as formyl, acetyl, 5-amino-5-carboxy-valeryl, wherein the amino group and the carboxyl group can be protected, phenylacetyl, phenoxyacetyl, thienylacetyl or furylacetyl, and carboxyl and/or functional groups present in the acyl radical are optionally in a protected form, with a phosporus pentahalide, especially phosphorus pentachloride, in the presence of a base, such as pyridine. The resulting 1-halogeno-methyleneimino compound either can be acylated direct or can be converted by treatment with an alcohol, such as methanol, into the corresponding 1-alkoxy-methylene compound, which is optionally substituted in the 1-position, and this compound is also usually acylated without being isolated.

The new compounds I can also be obtained when a 7β-[D-2-amino-2-(lower alkylsulphonylamino-phenyl)-acetylamino]-3-R-2-cephem-4ξ-carboxylic acid (VIII), wherein 2-amino and/or carboxyl can optionally be in a protected form and/or lower alkylsulphonylamino can optionally be in a N-acylated form, is isomerised and, if necessary or desired, the additional measures are carried out.

The amino and/or carboxyl group in a starting material can be in a protected form, for example as indicated and amino can preferably be in an acylated form and carboxyl can usually be in an esterified form.

The isomerisation can be carried out in a manner which is in itself known.

Thus, it is possible to isomerise a 2-cephem compound VIII by treating it with a basic agent and to isolate the corresponding 3-cephem compound from an equilibrium mixture of the 2-and 3-cephem compounds which may be obtained.

Suitable isomerising agents are, for example, organic nitrogen-containing bases, such as tertiary heterocyclic bases of aromatic character and above all tertiary aliphatic, aza-cycloaliphatic or araliphatic bases, especially N,N,N-tri-lower alkylamines, for example trimethylamine, triethylamine or N,N-diisopropyl-N-ethylamine, or mixtures of such bases, such as a mixture of a base of the pyridine type, for example pyridine, and a N,N,N-tri-lower alkylamine, for example pyridine and triethylamine. Furthermore, inorganic or organic salts of bases, especially of medium-strength to strong bases, with weak acids, such as alkali metal salts or ammonium salts of lower triethylammonium acetate or N-methylpiperidine acetate, and also other analogous bases or mixtures of such basic agents, can also be used.

The above isomerisation with basic agents can be carried out, for example, in the presence of a derivative of a carboxylic acid which is suitable for forming a mixed anhydride, such as a carboxylic acid anhydride or carboxylic acid halide, for example with pyridine in the presence of acetic anhydride. The reaction is preferably carried out in an anhydrous medium, in the presence or absence of a solvent, it being possible for bases which are used as reactants and are liquid under the reaction conditions at the same time also to serve as the solvent, and, if necessary, with cooling or heating, preferably in a temperature range of about −30° C to about +100° C, in an inert gas atmosphere, for example a nitrogen atmosphere, and/or in a closed vessel.

The 3-cephem compounds which are thus obtainable can be separated off, in a manner which is in itself known, from any 2-cephem compounds VIII which may still be present, for example by adsorption chromatography and/or crystallisation.

The isomerisation of 2-cephem compounds VIII can also be carried out by oxidising the latter in the 1-position, whereupon rearrangement of the 2-cephem compound into a 3-cephem compound takes place, and, if desired, separating a mixture of isomers, which is obtainable, of the 1-oxides of 3-cephem compounds and reducing the 1-oxides, which are thus obtainable, of the corresponding 3-cephem compounds.

Suitable oxidising agents which can be used for the oxidation of 2-cephem compounds VIII in the 1-position are suitable inorganic or organic per-acids or mixtures of hydrogen peroxide and acids, especially organic carboxylic acids which have a dissociation constant of at least $10^{-5}$. Suitable inorganic per-acids are periodic acid and persulphuric acid. Organic per-acids are corresponding percarboxylic acids and pesulphonic acids, which can be added as such or can be formed in situ by using at least one equivalent of hydrogen peroxide and of a carboxylic acid. It is appropriate to use a large excess of the carboxylic acid if, for example, acetic acid is used as the solvent. Suitable per-acids are, for example, performic acid, peracetic acid, pertrifluoracetic acid, permaleic acid, perbenzoic acid, monoperphthalic acid or p-toluenepersulphonic acid. The oxidation can also be carried out using hydrogen peroxide with catalytic amounts of an acid which has a dissociation constant of at least $10^{-5}$, such as acetic acid, perchloric acid or trifluoracetic acid.

The above oxidation is carried out in a manner which is in itself known, if necessary in the presence of catalysts, and under mild conditions, for example at temperatures of from about $-50°$ C to about $+100°$ C, and preferably from about $-10°$ C to about $+40°$ C.

The oxidation of 2-cephem compounds to the 1-oxides of the corresponding 3-cephem compounds can also be carried out by treatment with organic hypohalite compounds, such as lower alkyl hypochlorites, for example tert.-butyl hypochlorite, which are used in the presence of inert solvents, such as optionally halogenated hydrocarbons, for example methylene chloride, and at temperatures of from about $-10°$ C to about $+30°$ C, with periodate compounds, such as alkali metal periodates, for example potassium periodate, which are preferably used in an aqueous medium at a pH value of about 6 and at temperatures of from about $-10°$ C to about $+30°$ C, with iodobenzene dichloride, which is used in an aqueous medium, preferably in the presence of an organic base, for example pyridine, and with cooling, for example at temperatures of from about $-20°$ C to about $0°$, or with any other oxidising agent which is suitable for converting a thio grouping into a sulphoxide grouping.

A mixture, which may be obtained, of the α- and β-1-oxide isomers can be separated, for example by chromatography.

The reduction of the 1-oxides of 3-cephem compounds can be carried out in a manner which is in itself known, by treatment with a reducing agent, if necessary in the presence of an activating agent. Reducing agents which can be used are: catalytically activated hydrogen; reducing tin, iron, copper or magnesium cations, which are used in the form of corresponding compounds or complexes of an inorganic or organic nature, for example as tin-II chloride, copper-I chloride or manganese-II chloride, or as complexes, for example with ethylenediaminetetraacetic acid or nitrilotriacetic acid; reducing dithionite, iodide or ferrocyanide anions, which are used in the form of corresponding inorganic or organic salts, such as an alkali metal dithionite, iodide or ferrocyanide, or in the form of the corresponding acids; reducing trivalent inorganic or organic phosphorus compounds, such as phosphines, and also esters, amides and halides of phosphinous, phosphonous or phosphorous acid, and also the phosphorus-sulphur compounds which correspond to these phsophorus-oxygen compounds, wherein organic radicals above all represent lower alkyl or phenyl, for example triphenylphosphine, methyl diphenylphosphinite, diphenylchlorophosphine, dimethyl benzenephosphonite, trimethyl phosphite, phosphorus trichloride or phosphorus tribromide and the like; reducing halogenosilane compounds which contain at least one hydrogen atom bonded to the silicon atom and which, in addition to halogen, for example chlorine, can also contain organic radicals, such as lower alkyl or phenyl, such as chlorosilane, di- or tri-chlorosilane, diphenylchlorosilane, dimethylchlorosilane and the like; reducing quaternary chloromethyleneiminium halides, wherein the iminium group is substituted by one bivalent organic radical or two monovalent organic radicals, such as lower alkylene or lower alkyl, such as N-chloromethylene-N,N-diethyliminium chloride or N-chloromethylene-pyrrolidinium chloride; and complex metal hydrides, such as sodium borohydride, for example in the presence of suitable activating agents, such as cobalt-II chloride; and also borane dichloride.

Activating agents which may be mentioned and are used together with those of the abovementioned reducing agents which do not themselves display Lewis acid properties, that is to say which above all are employed together with the dithionite, iodide or ferricyanide reducing agents and the trivalent phosphorus reducing agents which do not contain halogen, or in the case of catalytic reduction, are, in particular, organic carboxylic acid halides and sulphonic acid halides, and also sulphur halides, phosphourus halides or silicon halides which have a second order hydrolysis constant equal to, or greater than, that of benzoyl chloride, for example phosgene, oxalyl chloride, acetyl chloride, 4-toluenesulphonyl chloride, methanesulphonyl chloride, thionyl chloride, phosphorus oxychloride, phosphorus trichloride, dimethylchlorosilane or trichlorosilane, and also suitable acid anhydrides, such as trifluoroacetic anhydride, or cyclic sultones, such as ethanesultone, 1,3-propanesultone, 1,4-butanesultone or 1,3-hexanesultone.

The reduction is preferably carried out in the presence of solvents or mixtures thereof and the choice of solvent is determined above all by the solubility of the starting materials and the choice of the reducing agent; solvents used are thus, for example, lower alkanecarboxylic acids or esters thereof, in the case of catalytic reduction, and, for example, optionally substituted, such as halogenated or nitrated, aliphatic, cycloaliphatic, aromatic or araliphatic hydrocarbons, for example methylene chloride, lower alkanecarboxylic acid esters or nitriles, for example ethyl acetate or acetonitrile, or or amides of inorgainc or organic acids, for example dimethylformamide or hexamethylphosphoric acid amide, or ethers, for example diethyl ether, tetrahydrofurane or dioxane, and ketones, for example acetone, and the like and these solvents preferably do not contain any water. The reaction is usually carried out at temperatures of from about $-20°$ C to about 100° C, it being possible to carry out the reaction at lower temperatures when highly reactive activating agents are used.

The starting materials VIII can be manufactured in a manner which is in itself known, for example when a 7β-acylamino-3-R-3-cephem-4-carboxylic acid (IX), wherein acyl represents an acyl radical which can be split off and which differs from D-2-amino-2-(lower alkylsulphonylamino-phenyl)acetyl (which optionally has protected 2-amino and N-acylated lower alkylsulphonylamino), and carboxyl and/or functional groups present in the acyl radical are optionally in a protected form, is isomerised to the corresponding 2-cephem compound (for example by treatment with a suitable base) and, in this compound, the acyl radical is split off, for example by treatment with phosphorus pentachloride in the presence of pyridine, followed by methanol and, optionally, water. The free amino group is then acylated with a D-2-amino-2-(lower alkylsulphonylamino-phenyl)-acetyl radical (which preferably has a protected 2-amino group and/or an optionally N-acylated lower alkylsulphonylamino group) by treatment with a D-2-amino-2-(lower alkylsulphonylamino-phenyl)-acetic acid (VII), wherein 2-amino is preferably in a protected form and/or lower alkylsulphonylamino is optionally in a N-acylated form, or with a reactive derivative, especially an anhydride, and preferably a mixed anhydride, thereof, such as a corresponding acid chloride or anhydride with a formic acid lower alkyl ester.

The starting materials VIII, wherein R represents lower alkoxy and wherein carboxyl and 2-amino are preferably in a protected form and lower alkylsulphonylamino is optionally in a N-acylated form, can also be formed by the basic cyclisation reaction, which is described in the text which follows, of a 2-{3-[D-amino-2-(lower alkylsulphonylamino-phenyl)-acetylamino]-4-$R_o$-thio-2-oxo-1-azetidinyl}-3-crotonic acid (X), wherein the carboxyl group and the 2-amino group are preferably in a protected form and the lower alkylsulphonylamino group is optionally in a N-acylated form.

The new compounds I, wherein R represents lower alkoxy, can also be obtained when a 2-[3-[D-2-amino-2-(lower alkylsulphonylamino-phenyl)-acetylamino]-4-$R_o$-thio-2-oxo-1-azetidinyl]-3-R-crotonic acid (X), wherein the carboxyl group is in a protected form or in the form of a halogenocarbonyl group, for example a chlorocabonyl group, the 2-amino group is preferably in a protected form and the lower alkylsulphonylamino group is optionally in a N-acylated form, R represents lower alkoxy and $R_o$ represents a leaving group, is cyclised by treatment with a base, and, if necessary, or desired, the additional measures are carried out.

In a starting material X, the lower alkoxy group R can be in the trans-position (crotonic acid configuration) or in the cis-position (isocrotonic acid configuration) relative to the carboxyl group.

In a starting material X, in which the carboxyl group and the amino group can be protected in a manner which is in itself known, for example as described above, and the lower alkylsulphonylamino group can optionally be N-acylated, a leaving group $R_o$ is, for example, a —S—$R_o^a$ group, a —SO$_2$—$R_o^b$ group, which is bonded by the sulphur atom to the thio sulphur, or a —S—SO$_2$—$R_o^b$ group.

In the group —S—$R_o^a$, $R_o^a$ is an optionally substituted monocyclic or bicyclic heterocyclic radical of aromatic character, which contains at least one ring nitrogen atom and optionally a further ring hetero-atom, such as oxygen or sulphur, and which is bonded to the thio sulphur by one of its ring carbon atoms, which is bonded to a ring nitrogen atom by means of a double bond. Such radicals can optionally be substituted, for example by lower alkyl, such as methyl or ethyl, lower alkoxy, such as methoxy or ethoxy, halogen, such as fluorine or chlorine, or aryl, such as phenyl.

Such radicals $R_o^a$ are, for example, monocyclic five-membered thiadiazacyclic, thiatriazacyclic, oxadiazacyclic or oxatriazacyclic radicals of aromatic character, but especially monocyclic five-membered diazacyclic, oxazacyclic and thiazacyclic radicals of aromatic character, or, above all, the corresponding benzdiazacyclic, benzoxazacyclic or benzthiazacyclic radicals, wherein the heterocyclic part is five-membered and is of aromatic character, it being possible, in such radicals, for a ring nitrogen atom which can be substituted to be optionally substituted, for example by lower alkyl, such as methyl. Examples of such groups are 1-methyl-2-imidazolyl, 2-thiazolyl, 1,3,4-thiadiazol-2-yl, 1,3,4,5-thiatriazol-2-yl, 2-oxazolyl, 1,3,4-oxadiazol-2-yl, 1,3,4,5-oxatriazol-2-yl, 2-quinolinyl, 1-methyl-2-benzimidazolyl, 2-benzoxazolyl and, in particular, 2-benzthiazolyl.

A $R_o^a$ group can also represent the acyl radical of an organic carboxylic acid or thiocarboxylic acid and be an optionally substituted, aliphatic, cycloaliphatic, araliphatic, aromatic or heterocyclic acyl or thioacyl radical. Such radicals are, inter alia, lower alkanoyl, for example acetyl or propionyl, lower thioalkanoyl, for example thioacetyl or thiopropionyl, cycloalkylcarbonyl, for example cyclohexylcarbonyl, cycloalkylthiocarbonyl, for example cyclohexylthiocarbonyl, benzoyl, thiobenzoyl, naphthoyl, naphthylthiocarbonyl, pyridoyl, for example 2-, 3- or 4-pyridoyl, thenoyl, for example 2- or 3-thenoyl, furoyl, for example 2- or 3-furoyl, or pyridylthiocarbonyl, for example 2-, 3- or 4-pyridylthiocarbonyl, or corresponding substituted acyl or thioacyl groups, for example acyl or thioacyl groups which are monosubstituted or polysubstituted by lower alkyl, such as methyl, halogen, such as fluorine or chlorine, lower alkoxy, such as methoxy, aryl, such as phenyl, or aryloxy, such as phenoxy.

In the groups —SO$_2$—$R_o^b$ and —S—SO$_2$—$R_o^b$, $R_o^b$ is an optionally substituted, especially aliphatic, cycloaliphatic, araliphatic or aromatic hydrocarbon radical. Suitable groups $R_o^b$ are, for example, optionally substituted, such as lower alkoxy-, for example methoxy-, halogen-, for example fluorine-, chlorine- or bromine-, aryl-, for example phenyl-, or aryloxy-, for example phenoxy-, monosubstituted or polysubstituted alkyl, especially lower alkyl, such as methyl, ethyl or butyl, alkenyl, such as lower alkenyl, for example allyl or butenyl, cycloalkyl, such as cyclopentyl or cyclohexyl, or naphthyl or, especially, phenyl, which are optionally monosubstituted or polysubstituted, for example by lower alkyl, for example methyl, lower alkoxy, for example methoxy, halogen, for example fluorine, chlorine or bromine, aryl, for example phenyl, aryloxy, for example phenoxy, or nitro, such as phenyl, 2-, 3- or, preferably, 4-tolyl, 2-, 3- or, preferably, 4-methoxyphenyl, 2-, 3- or 4-chlorophenyl, 4-biphenylyl, 4-phenoxyphenyl, 4-nitrophenyl or 1- or 2-naphthyl.

Suitable bases for the cyclisation reaction are, in particular, strong organic or inorganic bases. Bases to be singled out are, in particular, bicyclic amidines, such as corresponding diazabicycloalkenes, for example 1,5-diazabicyclo[4.3.0]non-5-ene or 1,5-diazabicyclo[5.4.0-

]undec-5-ene, and also substituted guanidines, for example guanidines polysubstituted by lower alkyl, such as methyl, such as tetramethylguanidine, and also metal bases, such as alkali metal hydrides, amides or alcoholates, especially lower alkanolates, for example the hydrides, amides or alcoholates, especially lower alkanolates, of lithium, sodium or potassium, for example sodium hydride, lithium di-lower alkylamides, such as lithium diisopropylamide, or potassium lower alkanolates, such as potassium tert.-butylate. Starting materials X, wherein the carboxyl group is in the form of a halogenocarbonyl group, for example a chlorocarbonyl group, can also be cyclised by treatment with a tertiary organic nitrogen base, for example a tri-lower alkylamine, such as triethylamine, and in the presence of an alcohol, such as a suitable lower alkanol, for example tert.-butanol, it is possible to obtain the corresponding ester of a compound I.

The reaction according to the invention is carried out in the presence of a suitable inert solvent, for example in an optionally halogenated, for example chlorinated, aliphatic, cycloaliphatic or aromatic hydrocarbon, such as hexane, cyclohexane, benzene, toluene or methylene chloride, an ether, such as a di-lower alkyl ether, for example diethyl ether, a di-lower alkoxy-lower alkane, such as dimethoxyethane, or a cyclic ether, such as dioxane or tetrahydrofurane, or also a lower alkanol, for example methanol, ethanol or tert.-butanol, or in a mixture thereof, at room temperature or, if necessary, with slight warming, for example up to about 50° C, and, if desired, in an inert gas atmosphere, such as a nitrogen atmosphere.

When a starting material X, wherein $R_o$ denotes a $—S—R_o^a$ group, for example the 2-benzthiazolylthio radical, is treated with one of the said bases, for example with 1,5-diazabicyclo[5.4.0]undec-5-ene, it is possible to increase the yield by adding a sulphinic acid of the formula $H—SO_2—R_o^b$, for example p-toluenesulphinic acid.

In the cyclisation reaction according to the invention it is possible, depending on the starting material and the reaction conditions, to obtain a single 3-cephem compound or a mixture thereof with the corresponding 2-cephem compound. Resulting mixtures can be separated in a manner which is in itself known with the aid of separation procedures, for example by adsorption and fractional elution, including chromatography (column, paper or plate chromatography) using suitable adsorbents, such as silica gel or aluminium oxide, and eluants, and also by fractional crystallisation, solvent partition and the like.

The starting materials X can be obtained, for example, when a 6-acylamino-2,2-dimethyl-penam-3-carboxylic acid XI, wherein acyl represents a D-2-amino-2-(lower alkylsulphonylamino)-acetyl radical, in which the 2-amino group is preferably in a protected form and the lower alkylsulphonylamino group can be N-acylated, or any other removable acyl radical of an organic carboxylic acid, in which case any functional groups which may be present in such a radical are preferably in a protected form, and wherein the carboxyl group is in a protected form, is converted, in a manner which is in itself known, for example by treatment with a percarboxylic acid, such as 3-chloroperbenzoic acid, into the corresponding 1-oxide. A 2-(3-acylamino-4-$R_o$-thio-2-oxo-1-azetidinyl)-3-methyl-3-butenoic acid XVI, wherein $R_o$ represents a $—S—R_o^a$, $—SO_2—R_o^b$ or $—S—SO_2—R_o^b$ radical is obtained from the above 1-oxide by reaction with a mercaptan of the formula $HS—R_o^a$ (XII), with a sulphinic acid of the formula $H—SO_2—R_o^b$ (XIII) or with a corresponding cyanide of the formula $N≡C—SO_2R_o^b$ (XIV), the latter preferably being employed in the presence of a quaternary ammonium halide, or with a thiosulphonic acid of the formula $HS—SO_2R_o^b$ (XV).

Compounds XVI, wherein $R_o$ denotes a $—SO_2—R_o^b$ or $—S—SO_2—R_o^b$ radical, can also be obtained when a compound XVI, wherein $R_o$ represents a $R_o^a$ radical, is reacted with a corresponding heavy metal sulphinate or heavy metal thiosulphinate, wherein the preferred heavy metals are, for example, monovalent or divalent cations of copper, mercury, silver or tin. These heavy metal salt reagents can optionally be formed in situ from the corresponding sulphinic or thiosulphonic acids, or readily soluble salts thereof, by reaction with a suitable heavy metal salt, such as copper-II sulphate, mercury-II diacetate, silver nitrate or tin-II chloride.

In a 3-butenoic acid compound XVI, wherein the carboxyl group is in a protected form, the terminal vinylene grouping is converted by oxidation, preferably by treatment with ozone, into the corresponding ozonide and this is decomposed, at the same time or subsequently, by reaction with a suitable reducing agent, such as an alkali metal bisulphite, for example sodium bisulphite, a di-lower alkyl sulphide, for example dimethyl sulphide, a phosphine, for example triphenylphosphine, or tetracyanoethylene. In this way 2-(3-acylamino-4-$R_o$-thio-2-oxo-1-azetidinyl)-3-hydroxycrotonic acid (XVII), wherein the carboxyl group is in a protected form and $R_o$ has the abovementioned meaning, is obtained. The hydroxyl group can now be etherified in a manner which is in itself known, for example as described above, for example by treatment with a diazolower alkane, a suitable reactive ester of a lower alkanol, such as a corresponding sulphate, halogenosulphate or sulphonate, with a tri-lower alkyl-oxonium, di-lower alkylcarbenium or di-lower alkylhalonium salt, such as the hexafluoroantimonate, hexafluorophosphate or tetrafluoborate, or with a 1-lower alkyl-triazene compound substituted in the 3-position, such as a 1-lower alkyl-triazene compound substituted in the 3-position by 4-methyl-phenyl, and converted into the desired lower alkoxy group.

If necessary, it is possible at any suitable stage of the manufacture of a starting material X to split off an acyl group which differs from D-2-amino-2-(lower alkylsulphonylamino-phenyl)-acetyl, for example by treatment with phosphorus pentachloride in the presence of pyridine, followed by methanol and, optionally, water, and to acylate the free amino group of an intermediate product, which is thus obtainable, with a D-2-amino-2-(lower alkylsulphonylamino-phenyl)-acetyl radical, wherein 2-amino is preferably in a protected form and lower alkylsulphonylamino is optionally in a N-acylated form, by treatment with the corresponding acid or a reactive derivative, such as an anhydride, preferably a mixed anhydride, for example the chloride, thereof. Furthermore, it is possible, at the suitable stages, to convert a radical $R_o$ into another radical $R_o$ and/or to convert a group which is present in the free form or a protected form into a protected form or the free form, or into another protected form.

The new compounds I can also be obtained when a 7β-[D-2-amino-2-(aminophenyl)-acetylamino]-3-R-3-cephem-4-carboxylic acid (XVIII), wherein the 2-amino group is in a protected form, the carboxyl group is optionally in a protected form and the amino group on the phenyl ring is optionally in a reactive protected form, that is to say in a form which permits sulphonylation, for example the acylated form, is treated with a lower alkanesulphonic acid or a reactive functional derivative thereof and, if necessary or desired, the additional measures are carried out.

In a starting material XVIII, the carboxyl group can be protected, preferably in an esterified form, for example as described above, and above all in the form of a silyl ester, such as a trimethylsilyl ester (which usually is manufactured immediately prior to the acylation reaction by treatment with a corresponding silylating agent, for example trimethylchlorosilane or bis-(trimethylsilyl)-acetamide). The carboxylic acid starting material XVIII can, however, also be employed in the form of a salt, for example in the form of an ammonium salt, such as in the form of a triethylammonium salt, or in a protected form, which is obtainable by reacting the carboxylic acid starting material XVIII with a suitable organic phosphorus halide compound, such as with a lower alkyl- or lower alkoxy-phosphorus dihalide, such as methyl-phosphorus dichloride, ethyl-phosphorus dibromide or methoxy-phosphorus dichloride. An amino group, on the phenyl ring, which is in a reactive protected form is, for example, an amino group protected by a silyl radical, such as one of the corresponding radicals mentioned above, or also one of the abovementioned acylated amino groups, for example the tert.-butoxyamino group.

The sulphonylation of the free amino group, or the reactive protected amino group, in the starting material XVIII is carried out in a manner which is in itself known. Sulphonylating agents which can be used are lower alkylsulphonic acids or reactive derivatives thereof.

If a free lower alkylsulphonic acid is employed for the sulphonylation, suitable condensing agents, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium 3'-sulphonate and N-tert.-butyl-5-methyl-isoxazolinium perchlorate, or a suitable acylamino compound, for example 2-ethoxy-1-ethoxycarbonyl-1,2-dihydroquinoline, are customarily used. The condensation reaction is preferably carried out in an anhydrous reaction medium, for example in methylene chloride, dimethylformamide or acetonitrile.

A functional derivative of a lower alkylsulphonic acid is, above all, an anhydride thereof, including, and preferably, a mixed anhydride. Mixed anhydrides are, for example, those with inorganic acids, especially with hydrogen halide acids, that is to say the corresponding sulphonic acid halides, for example the sulphonic acid chloride or sulphonic acid bromide, and also the anhydride with hydrazoic acid, that is to say the corresponding acid azide, with a phosphorus-containing acid, for example phosphoric acid or phosphorous acid, with a sulphur-containing acid, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl or isobutyl half-ester of carbonic acid, or with organic, especially aliphatic or aromatic, sulphonic acids, for example p-toluenesulphonic acid.

Further sulphonic acid derivatives which are suitable for reaction with the amino group in a starting material XVIII are activated esters of lower alkylsulphonic acids, which usually have a protected amino group, such as esters with vinylogous alcohols (that is to say enols), such as vinylogous lower alkenols, or aryl esters, such as phenyl esters, which are preferably substituted, for example by nitro or halogen, such as chlorine, for example pentachlorophenyl, 4-nitrophenyl or 2,4-dinitrophenyl esters, heteroaromatic esters, such as benztriazole esters, or diacyliminoesters, such as succinylimino- or phthalylimino-esters.

The sulphonylation with a sulphonic acid derivative, such as with an anhydride and especially with a sulphonic acid halide, can be carried out in the presence of an acidbinding agent, for example an organic base, such as an organic amine, for example a tertiary amine, such as a tri-lower alkylamine, for example triethylamine, a N,N-di-lower alkyl-aniline, for example N,N-dimethylaniline, or a base of the pyridine type, for example pyridine, an inorganic base, for example an alkali metal hydroxide, carbonate or bicarbonate or alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or 1,2-propylene oxide.

The above sulphonylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or in mixtures thereof, and, if necessary, at a lowered or elevated temperature, for example at about 0° to about 100° C, and/or in an inert gas atmosphere, for example a nitrogen atmosphere.

The starting materials (XVIII) can be obtained when the 7β-amino group in a 7β-amino-3-R-3-cephem-4-carboxylic acid (VI), wherein the carboxyl group is optionally in a protected form and the 7β-amino group is optionally in a reactive protected form, that is to say in a form which permits acylation, is acylated with D-2-amino-2-(Am-phenyl)-acetyl radical, wherein Am denotes a protected or masked amino group which can be converted into a free amino group and wherein the 2-amino group is protected, and, in a resulting 7β-[2-amino-2-(Am-phenyl)-acetylamino]-3-R-3-cephem-4-carboxylic acid, wherein the 2-amino group is in a protected form and the carboxyl group is optionally in a protected form, the group Am is optionally converted into a free amino group.

A group Am is, for example, a protected amino group which differs from the protected 2-amino in the way in which it is converted into a free amino group and which can be converted selectively into a free amino group, that is to say without simultaneously liberating the 2-amino group. Thus, for example, the 2-amino group can be protected by a tert.-butoxycarbonyl group and Am can denote a 2,2,2-trifluoroacetoxycarbonylamino group, and in this case the latter can be split into a free amino group using zinc and acetic acid, whilst the 2- tert.-butoxycarbonylamino group remains intact under these conditions. Further such pairs of amino protective groups, and the methods for their selective splitting, can be taken from the description of the additional measures which is given further below. Masked amino groups Am are, for example, the azido group and, in particular, the nitro group.

The acylation of the 7β-amino-3-R-3-cephem-4-carboxylic acid VI, wherein the functional groups are protected as indicated, is carried out in a manner which is in itself known with D-2-amino-2-(Am-phenyl)-acetic acid, wherein the amino groups are, as indicated, in a protected or masked form, or with a reactive functional derivative thereof, for example an anhdride, such as a corresponding acid chloride, as has been indicated above for the acylation of protected compounds VI with protected D-2-amino-2-(lower alkylsulphonylamino-phenyl)-acetic acids VII, or their reactive functional derivatives.

The choice of the carbonyl protective group and of the 2-amino protective group in the starting material VI depends, as indicated above, on the protected or masked amino group Am which is to be used. The conversion of these groups Am in a resulting acylated compound XVIII into a free amino group is carried out in a manner which is in itself known, as indicated further below for the conversion of protected and masked amino groups. A nitro group Am can, analogously to an azido group, be converted into a free amino group by reduction.

In the compounds obtainable according to the invention, protected carboxyl and/or amino groups and/or N-acylated lower alkylsulphonylamino groups are optionally liberated at the same time in a manner which is in itself known, such as by means of solvolysis, including hydrolysis, alcoholysis or acidolysis, or by means of reduction, including hydrogenolysis or chemical reduction.

Thus, for example, a tert.-lower alkoxycarbonyl, polycycloalkoxycarbonyl or diphenylmethoxycarbonyl group can be converted into a free carboxyl group by treatment with a suitable acid agent, such as formic acid or trifluoroacetic acid, optionally with the addition of a nucleophilic compound, such as phenol or anisole. An optionally substituted benzyloxycarbonyl group can, for example, be liberated by means of hydrogenolysis by treatment with hydrogen in the presence of a hydrogenation catalyst, such as a palladium catalyst. Furthermore, certain substituted benzyloxycarbonyl groups, such as 4-nitrobenzyloxycarbonyl, can also be converted into a free carboxyl group by means of chemical reduction, for example by treatment with an alkali metal dithionite, for example sodium dithionite, or with a reducing metal, for example zinc, or a metal salt, such as a chromium-II salt, for example chromium-II chloride, usually in the presence of a hydrogen donor, which, together with the metal, is able to produce nascent hydrogen, such as an acid, above all acetic acid, and also formic acid, or an alcohol, in which case water is preferably added. By means of treatment with a reducing metal or metal salt, as described above, it is also possible to convert a 2-halogeno-lower alkoxycarbonyl group (optionally after converting a 2-bromo-lower alkoxycarbonyl group into a 2-iodo-lower alkoxycarbonyl group) or an acylmethoxycarbonyl group into a free carboxyl group, and an aroylmethoxycarbonyl group can also be split by treatment with a nucleophilic, preferably salt-forming, reagent, such as sodium thiophenolate or sodium iodide. A carboxyl group protected, for example, by silylation can be liberated in the customary manner, for example by treatment with water or an alcohol. Analogously, a carboxyl group protected by reaction with an organic phosphorus halide compound can also be libertated by hydrolysis or alcoholysis.

A protected amino group is liberated in a manner which is in itself known and which differs depending on the nature of the protective group, for example by means of solvolysis or reduction. A 2-halogeno-lower alkoxycarbonylamino group (optionally after converting a 2-bromo-lower alkoxycarbonyl group into a 2-iodo-lower alkoxycarbonyl group), an acylmethoxycarbonylamino group or, for example, a 4-nitrobenzyloxycarbonylamino group can be liberated, for example, by treatment with a suitable chemical reducing agent, such as zinc in the presence of aqueous acetic acid, an arolmethoxycarbonylamino group can also be liberated by treatment with a nucleophilic, preferably salt-forming, reagent, such as sodium thiophenolate, and a 4-nitrobenzyloxycarbonylamino group can also be liberated by treatment with an alkali metal dithionite, for example sodium dithionite, a diphenylmethoxycarbonylamino, tert.-lower alkoxycarbonylamino or polycycloalkoxycarbonylamino group can be liberated by treatment with, for example, formic acid or trifluoroacetic acid, an optionally substituted benzyloxycarbonylamino group can be liberated, for example, by means of hydrogenolysis by treatment with hydrogen in the presence of a hydrogenation catalyst, such as a palladium catalyst, an arylthioamino or aryl-lower alkylthioamino group can be liberated, for example, by treatment with a nucleophilic reagent, such as sulphurous acid, an arylsulphonylamino group can be liberated, for example, by means of electrolytic reduction, a 1-acyl-2-lower alkylideneamino group or a triarylmethyl group can be liberated, for example, by treatment with an aqueous mineral acid and an amino group protected by an organic silyl group can be liberated, for example, by means of hydrolysis or alcoholysis.

An amino group protected in the form of an azido group is converted into a free amino group in a manner which is in itself known, by reduction, for example by catalytic hydrogenation with hydrogen and a hydrogenation catalyst, such as platinum oxide, palladium or Raney nickel, or by means of zinc and an acid, such as acetic acid. The catalytic hydrogenation is preferably carried out in an inert solvent, such as a halogenated hydrocarbon, for example methylene chloride, or also in water or a mixture of water and an organic solvent, such as an alcohol or dioxane, at about 20° to 25°, or also at a lowered or elevated temperature.

A N-acylated lower alkylsulphonylamino group is also converted into a lower alkylsulphonylamino group in a manner which is in itself known, for example by solvolysis or reduction. The methods which can be used to split off these N-acyl groups are the same as those indicated for splitting off acyl groups, for example 2-halogeno-lower alkoxycarbonyl, acylmethoxycarbonyl, 4-nitrobenzyloxy-carbonyl, aroylmethoxycarbonyl, diphenylmethoxycarbonyl, tert.-lower alkoxycarbonyl, polycycloalkoxycarbonyl, benzyloxycarbonyl or arylsulphonyl, from corresponding acylamino groups.

Salts of the new compounds I can be manufactured in a manner which is in itself known. Thus, salts can be formed, for example, by treatment with metal compounds, such as alkali metal salts of suitable carboxylic acids, for example the sodium salt of α-ethyl-caproic acid, or with ammonia or a suitable organic amine, preferably using stoichiometric amounts or only a small excess of the salt-forming agent. Acid addition salts are obtained in the customary manner, for example by treatment with an acid or a suitable anion exchange reagent. Inner salts can be formed, for example, by neutralising, for example, salts, such as acid addition salts, to the isoelectric point, for example with weak bases, or by treatment with liquid ion exchangers.

Resulting salts can be converted into the free compounds in the customary manner, metal salts and ammonium salts, for example, by treatment with suitable acids, and acid addition salts, for example, by treatment with a suitable basic agent.

The process also comprises those embodiments according to which compounds arising as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds mentioned initially as being particularly preferred are obtained.

The new compounds of the present invention can, for example, be used for the manufacture of pharmaceutical formulations which contain an effective amount of the active substance together with, or mixed with, inorganic or organic, solid or liquid, pharmaceutically usable excipients which are suitable for enteral or parenteral administration. Thus, tablets or gelatine capsules are used which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone, and, if desired, disintegrating agents, for example starches, agar, alginic acid or a salt thereof, such as sodium alginate, and/or effervescent mixtures, or adsorbents, dyestuffs, flavourings and sweeteners. Furthermore, the new pharmacologically active compounds can be used in the form of injectable formulations, for example formuations which can be administered intravenously, or of infusion solutions. Such solutions are preferably isotonic aqueous solutions or suspensions and these can, for example, be manufactured before use from lyophilised formulations which contain the active compound on its own or together with an excipient, for example mannitol. The pharmaceutical formulations can be sterilised and/or contain auxiliaries, for example preservatives, stabilisers, wetting agents and/or emulsifiers, solubilising agents, salts for regulating the osmotic pressure and/or buffers. The present pharmaceutical formulations which can, if desired, contain further pharmacologically valuable substances, are manufactured in a manner which is in itself known, for example by means of conventional mixing, granulating, dragee-making, dissolving or lyophilising processes, and contain from about 0.1% to 100%, and especially from about 1% to about 50%, of the active substance and lyophilisates contain up to 100% of the active substance. The individual dose for a warm-blooded animal about 70 kg in weight is between 0.1 and 0.75 g and the daily dose is between 0.2 and 1.0 g.

In the context of the present description, the organic radicals described as "lower" contain, unless expressly defined, up to 7, and preferably up to 4, carbon atoms.

The examples which follow serve to illustrate the invention; temperatures are given in degrees centigrade.

EXAMPLE 1 a. 1.04 ml of bis-(trimethylsilyl)-acetamide are added to a suspension of 0.764 g of finely powdered 7β-amino-3-methoxy-3-cephem-4-carboxyl acid hydrochloride, which contains one mol of dioxane, in 10 ml of absolute methylene chloride, under an argon atmosphere and at room temperature (the addition is effected in the course of about 10 minutes) and the mixture is stirred for 45 minutes.

0.34 ml of isobutyl chloroformate is added to a solution, which has been cooled to −15°, of 0.896 g of D-2-tert.-butoxycarbonylamino-2-(3-methylsulphonylamino-phenyl)-acetic acid and 0.29 ml of 4-methyl-morpholine in 10 ml of absolute methylene chloride, under an argon atmosphere, and the mixture is allowed to react for a further 15 minutes. The silylated starting material described above is added dropwise, at −10°, to the mixed anhydride which is thus obtainable and the reaction mixture is stirred for 15 minutes at −10°, for 15 minutes at 0° and for 15 minutes at room temperature It is then diluted with 100 ml of ethyl acetate and washed three times with a saturated aqueous solution of sodium chloride. The aqueous phases are again extracted with ethyl acetate and the combined organic solutions are dried over magnesium sulphate and freed from solvent under reduced pressure. The residue is purified over silica gel using a 1:1 mixture of methylene chloride and ethyl acetate as the eluant. 7β-[D-2-tert.-Butoxycarbonylamino-2-(3-methyl-sulphonylamino-phenyl)-acetylamino]-3-methoxy-3-cephem-4-carboxylic acid, which according to thin layer chromatography is a single compound, is obtained as an amorphous product; thin layer chromatogram (silica gel; identification with ninhydrin): $R_f \sim 0.63$ (system: sec.-butanol/acetic acid/water, 67:10:23), ultraviolet absorption spectrum (in 95% strength aqueous ethanol): $\lambda_{max} = 273$ nm ($\epsilon = 7,100$); infrared absorption spectrum (in methylene chloride): characteristic bands at 3,380, 2,930, 1,765, 1,685, 1,605, 1,485 and 1,160.

The same compound can also be obtained as follows:

ai. 7.52 ml of bis-(trimethylsilyl)-acetamide are added to a suspension of 6.22 g (27 mmols) of finely powdered 7β-amino-3-methoxy-3-cephem-4-carboxylic acid in 120 ml of absolute methylene chloride, under an argon atmosphere and at room temperature, (the addition is effected in the course of about 10 minutes) and the mixture is stirred for 45 minutes.

3.93 ml of isobutyl chloroformate are added to a solution, which has been cooled to −15°, of 10.33 g (30 mmols) of D-2-tert.-butoxycarbonylamino-2-(3-methyl-sulphonylaminophenyl)-acetic acid and 3.33 ml of 4-methyl-morpholine in 180 ml of absolute acetonitrile, under an argon atmosphere, and the mixture is allowed to react for a further 25 minutes. The silylated starting material described above is added dropwise, at −15°, to the mixed anhdyride which is thus obtainable and the reaction mixture is stirred for 2 hours at 0° and for 30 minutes at room temperature. The solvent is then removed in a rotary evaporator and the residue is taken up in 400 ml of ethyl acetate and washed three times with a saturated aqueous solution of sodium chloride. The aqueous phases are again extracted with ethyl acetate. The combined organic solutions are dried over magnesium sulphate and freed from solvent under reduced pressure. The residue is purified over silica gel using a 1:1 mixture of methylene chloride and ethyl acetate as the eluant. 7β-[D-2-tert.-Butoxycarbonylamino-2-(3-methylsulphonylamino-phenyl)-acetylamino]-3-methoxy-3-cephem-4-carboxylic acid, which according to thin layer chromatography is a single compound, is obtained as an amorphous product which, when crystallised from 1:3 methylene chloride/-diethyl ether, has a melting point of 140° (decomposition). The physicochemical data are identical to those of Example 1a).

aii. 1.23 ml of N,O-bis-(trimethylsilyl)-acetamide are added to a suspension of 891 mg of 7-amino-3-methoxy-ceph-3-em-4-carboxylic acid in 10 ml of absolute methylene chloride and the mixture is stirred for 1 hour at 23° (solution A).

0.58 ml of isobutyl chloroformate is added to a solution of 1.58 g of D-2-tert.-butoxycarbonylamino-2-(3-methylsulphonylamino-phenyl)-acetic acid and 0.52 ml of N-methylmorpholine in 20 ml of acetonitrile, at −10° to −15°, and the mixture is stirred at this temperature for ½ hour (solution B).

Solution A is added rapidly, under nitrogen, to solution B, which has been cooled to −25° C, and the mixture is then stirred for 1½ hours at 0°.

The batch is stirred into 100 ml of a ⅓ M phosphate buffer which as a pH of 7 and the mixture is freed from organic solvents in vacuo. The residual aqueous solution is washed with ethyl acetate in order to remove the neutral constituents. The aqueous phase is covered with a layer of further ethyl acetate, acidifed to pH 2 with 85% strength phosphoric acid, cooled and saturated with sodium chloride. Phase separation and subsequent extraction with ethyl acetate gives an extract which, when dried over sodium sulphate and evaporated, gives 7β-[D-2-tert.-butoxycarbonyl-amino-2-(3-methylsulphonylamino-phenyl)-acetylamino]-3-methoxy-3-cephem-4-carboxylic acid, which in a thin layer chromatogram is a single compound, in the form of a pale beige foam. The compound can be crystallised accoring to Example 1 (ai).

The starting material can be obtained as follows:

b. 35 ml of dimethyldichlorosilane are added to a suspension of 1.17 g of 7β-phenoxyacetylamino-3-methoxy-3-cephem-4-carboxylic acid and 1.45 ml of N,N-dimethylaniline in 5.5 ml of absolute methylene chloride, under a nitrogen atmosphere and at 20°, and the mixture is then stirred for 30 minutes at the same temperature. The clear solution is cooled to −20°, 0.8 g of phosphorus pentachloride is added and the mixture is stirred for 30 minutes. At the same temperature, a mixture, which has been precooled to 31°°, of 0.45 ml of N,N-dimethylaniline and 0.45 ml of n-butanol is added in the course of 2 to 3 minutes and 10 ml of n-butanol, which has been precooled to −20°, are then added rapidly and the mixture is then stirred for 20 minutes at −20° and for 10 mintues without cooling. 0.2 ml of water is added at about −10°, the mixture is stirred in an ice bath (about 0°) for about 10 minutes, 5.5 ml of dioxane are then added and, after stirring for a further 10 minutes at 0°, about 2.25 ml of tri-n-butylamine are added in portions until samples diluted with water assume a constant pH value of 3.5. After stirring for 1 hour at 0°, the precipitate is filtered off, washed with dioxane and recrystallised from a mixture of water and dioxane. The hydrochloride of 7β-amino-3-methoxy-3-cephem-4-carboxylic acid, which is thus obtainable, contains one mol of dioxane and has a melting point of above 300°; thin layer chromatrogram: Rf 0.17 (silica gel; system n-butanol/carbon tetrachloride/methanol/-formic acid/water, 30:40:20:5:5).

EXAMPLE 2 a. In a manner analogous to Example (1a), treatment of the mixed anhydride, obtained from 0.448 g of D-2-tert.-butoxycarbonylamino-2-(3-methylsul-phonylamino-phenyl)-acetic acid and 0.17 ml of isobutyl chloroformate in the presence of 0.14 ml of 4-methylmorpholine and 5ml of methylene chloride at −15°, with trimethylsilyl 7β-amino-3-chloro-3-cephem-4-carboxylate, obtained from 0.24 g of 7β-amino-3-chloro-3-cephem-4-carboxylic acid and 0.5 ml of bis-(trimethylsilyl)-acetamide in 10 ml of methylene chloride, gives, by the process described above, 7β-[D-2-tert.-butoxycarbonylamino-2-(3-methylsul-phonylamino-phenyl)-acetylamino]-3-chloro-3-cephem-4-carboxylic acid.

ai. In a manner analogous to Example (1ai), treatment of the mixed anhydride, obtained from 1.55 g (4.5 mmols) in D-2-tert.-butoxycarbonylamino-2-(3-methyl-sulphonylamino-phenyl)-acetic acid and 0.6 ml of isobutyl chloroformate in the presence of 0.5 ml of 4-methylmorpholine and 25 ml of acetonitrile at −15°, with trimethylsilyl 7β-amino-3-chloro-3-cephem-4-carboxylate, obtained from 0.88 g (3.75 mmols) of 7β-amino-3-chloro-3-cephem-4-carboxylic acid and 1.05 ml of bis-(trimethylsilyl)-acetamide in 20 ml of methylene chloride, gives, by the process described above, 7β-[D-2-tert.-butoxycarbonylamino-2-(3-methylsul-phonylamino-phenyl)-acetylamino]-3-chloro-3-cephem-4-carboxylic acid; thin layer chromatogram (silica gel; identification with ninhydrin): Rf ~ 0.58 (system: sec.-butanol/acetic acid/water, 67:10:23), IR spectrum (in methylene chloride): characteristic bands at 3,390, 2,930, 1,775, 1,685, 1,485 and 1,160 cm$^{-1}$.

The starting material can be obtained as follows:

b. 1.59 g (4 mmols) of diphenylmethyl 7β-amino-3-chloro-3-cephem-4-carboxylate are dissolved in 5 ml of trifluoroacetic acid at 0° and the solution is stirred for 15 minutes. The clear, pale yellow solution is diluted with 20 ml of toluene and then freed from excess trifluoro-acetic acid and toluene under reduced pressure. The residue is dissolved in about 20 ml of water/ethyl acetate (1:1), the organic phase is separated off and the acid aqueous phase is brought to a pH of 3.0 with 20% strength triethylamine in methanol. The pale yellow precipitate is filtered off, washed with ethyl acetate and diethyl ether and dried under a high vacuum. 320 mg of 7β-amino-3-chloro-3-cephem-4-carboxylic acid are isolated as a pale yellow amorphous powder; thin layer chromatogram: Rf = 0.08 (silica gel, n-butanol/acetic acid/water, 67:10:23).

EXAMPLE 3

1.18 ml (9 mmols) of isobutyl chloroformate are added to a solution, which has been cooled to −15°, of 3.1 g (9 mmols) of D-2-tert.-butoxycarbonylamino-2-(3-methylsulphonylamino-phenyl)-acetic acid and 1.0 ml of 4-methylmorpholine in 50 ml of absolute acetonitrile, under an argon atmosphere and with the exclusion of moisture. After 30 minutes, 3.0 g (7.5 mmols) of diphenylmethyl 7β-amino-3-chloro-3-cephem-4-carboxylate, dissolved in 50 ml of absolute methylene chloride, are added, at −15°, to the mixed anhdyride thus obtained. The reaction mixture is stirred for 1½ hours at 0° and of 1¼ hours at room temperature. The solvents are then removed in a rotary evaporator. The residue is dissolved in 500 ml of ethyl acetate and washed three times with a saturated aqeuous solution of sodium chloride. The organic phase is dried over magnesium sulphate and freed from solvent under reduced pressure. The crude product is purified over 40 times the amount of silica gel using 1:1 methylene chloride/ethyl acetate as the eluant. Diphenylmethyl 7β-[D-2-tert.-butoxycarbonylamino-2-(3-methylsulphonylamino-phenyl)-acetylamino]-3-chloro-3-cephem-4-carboxylate, which according to thin layer chromatography is a single compound and which has a melting point of 184°–187° (from acetone/ether/petroleum ether, 1:2:2) is obtained; thin layer chromatogram (silica gel; identification with ninhydrin): Rf ∼ 0.52 (system: toluene/ethyl acetate, 1:1). IR spectrum (in methylene chloride): characteristic bands at 3,420, 1,790, 1,725, 1,700, 1,620 and 1,158 cm$^{-1}$.

EXAMPLE 4

In a manner analogous to Example 3, treatment of the mixed anhydride, obtained from 1.05 g (4.5 mmols) of D-2-tert.-butoxycarbonylamino-2-(3-methylsulphonylamino-phenyl)-acetic acid and 0.6 ml of isobutyl chloroformate in the presence of 0.5 ml of N-methylmorpholine in 25 ml of acetonitrile at −15°, with 1.49 g (3.75 mmols) of diphenylmethyl 7β-amino-3-methoxy-4-carboxylate, dissolved in 25 ml of methylene chloride, gives, by the process described above, diphenylmethyl 7β-[D-2-tert.-butoxycarbonylamino-2-(3-methylsulphonylamino-phenyl)-acetylamino]-3-methoxy-3-cephem-4-carboxylate: melting point 127°–130°; thin layer chromatogram: Rf ∼ 0.21 (silica gel; toluene/acetone, 3:1); IR spectrum (in methylene chloride): characteristic bands at 3,440, 1,787, 1,725, 1,705, 1,342 and 1,162 cm$^{-1}$.

EXAMPLE 5 a. 0.31 ml (4.22 mmols) of thionyl chloride and then 1.5 g (2.11 mmols) of diphenylmethyl 7β-[D-2-tert.-butoxycarbonylamino-2-(3-methylsulphonylamino-phenyl)-acetylamino]-3-hydroxy-3-cephem-4-carboxylate, dissolved in 6 ml of dimethylformamide, are added carefully dropwise, with the exclusion of moisture and under an argon atmosphere, to 6 ml of dimethylformamide, which has been cooled to 0°. The reaction mixture is brought to room temperature, stirred for a further 4 hours, then diluted with methylene chloride and washed twice with ice water and twice with a saturated aqueous solution of sodium chloride. The organic phase is dried (MgSO$_4$) and freed from solvent under reduced pressure. The residue, which is a yellow oil, is purified over 30 times the amount of silica gel using 4:1 toluene-/ethylacetate as the eluant and diphenylmethyl 7β-[D-2-tert.-butoxycarbonylamino-2-(3-methylsulphonylamino-phenyl)-acetylamino]-3-chloro-3-cephem-4-carboxylate is obtained; the physicochemical data of this product are identical to those of the product obtained according to Example 3.

The starting material can be prepared as follows:

b. 1.04 ml (4.16 mmols) of bis-trimethylsilyl-acetamide area added to a solution of 2.17 g (4.16 mmols) of diphenylmethyl 7β-amino-3-hydroxy-3-cephem-4-carboxylate in 25 ml of freshly distilled methylene chloride. The reaction mixture is stirred for 45 minutes at room temperature, under an argon atmosphere.

0.8 ml of isobutyl chloroformate is added to a solution which has been cooled to −15°, of 2.0 g (5.8 mmols) of D-2-tert.-butoxycarbonylamino-2-(3-methylsulphonylamino-phenyl)-acetic acid and 0.65 ml of N-methyl-morpholine in 24 ml of absolute methylene chloride, with the exclusion of moisture and under an argon atmosphere, and the mixture is allowed to react for a further 20 minutes at −15°. The silylated starting material, which has been described above and has been cooled to 31 10°, is added dropwise to the mixed anhydride thus obtained and the reaction mixture is then stirred for ½ hour, at 31 10° and for ½ hour at 0°. The reaction solution is then diluted with 100 ml of ethyl acetate and washed three times with a saturated aqueous solution of sodium chloride. After drying the organic phase (MgSO$_4$), the solvent is removed in a rotary evaporator. The oily residue is purified over 70 g of silica gel causing a 4:1 mixture of toluene/ethyl acetate as the eluant. Diphenylmethyl 7β-[D-2-tert.-butoxycarbonylamino-2-(3-methylsulphonylamino-phenyl)-acetylamino]-3-hydroxy-3-cephem-4-carboxylate, which according to thin layer chromatogaphy is a single compound, is obtained as an amorphous product; thin layer chromatogram: Rf ∼ 0.18 (silica gel; ethyl acetate); IR spectrum (in methylene chloride): characteristic bands at 3,380, 1,775, 1,685, 1,605, 1,485 and 1,160 cm$^{-1}$.

EXAMPLE 6

850 mg (1.2 mmols) of diphenylmethyl 7β[D-2-tert.-butoxycarbonylamino-2-(3-methylsulphonylamino-phenyl)-acetylamino]-3-hydroxy-3-cephem-4-carboxylate are dissolved in a mixture of 1 ml of carbon tetrachloride and 20 ml of methylene chloride, 520 mg (2.0 mmols) of triphenylphosphine are added at room temperature and the mixture is left to stand for 24 hours. The reaction mixture is diluted with 50 ml of methylene chloride and wahsed three times with a saturated solution of sodium chloride. The organic phase is dried (MgSo$_4$) and freed from solvent in a rotary evaporator. The residue, which is a yellow oil, is purified over 30 times the amount of silica gel using 1:1 toluene/ethyl acetate as the eluant and, after crystallisation from methylene chloride/ether, diphenylmethyl 7β-[D-2-tert.-butoxycarbonylamino-2-(3-methylsulphonylamino-phenyl)-acetylamino]-3-chloro-3-cephem-4-carboxylate which has a melting point of 126°–129° is obtained.

EXAMPLE 7 a. 0.12 ml (0.508 mmol) of bis-trimethylsilyl-acetamide is added to a solution of 400 mg (0.462 mmol) of diphenylmethyl 2-{4-(p-toluenesulphonylthio)-3-[D-2-tert.-butoxycarbonylamino-2-3-methylsulphonylamino-phenyl)-acetylamino]-2-oxoazetidin-1-yl}-3-hydroxycrotonate in 3 ml of 1,2-dimethoxyethane, under a nitrogen atmosphere, and the mixture is stirred for 1 hour at room temperature. The solution is evaporated completely and the oily residue is dried for 1 hour under a high vacuum. The silylated crude product is taken up in 3 ml of dried 1,2-dimethoxyethane and, after the solution has been cooled to 0° C, 0.075 ml (0.508 mmol) of 1,5-diazabicyclo[5.4.0]undec-5-ene is added. After a reaction time of 6 hours at 0° C under a nitrogen atmosphere, 0.3 ml of acetic acid is added and the mixture is diluted with methylene chloride. The methylene chloride solution is washed successively with dilute sulphuric acid, water and dilute bicarbonate solution. The aqueous phases are extracted with methylene chloride and the combined organic phases are dried with sodium sulphate, concentrated in vacuo and dried under a high vacuum. Crude diphenylmethyl 7β-[D-2-tert.-butoxycarbonylamino-2-(3-methylsulphonylamino-phenyl)-acetylamino[-3-hydroxy-3-cephem-4-carboxylate is obtained.

b. An excess of an etheral solution of diazomethane is added, at 0° C, to a solution of the crude product in chloroform and the mixture is left to stand for 5 minutes at 0° C. It is then concentrated completely and the oily residue is chromatographed on silcia gel thick layer plates (toluene/ethyl acetate, 3:1). Diphenylmethyl 7β-[D-2-tert.-butoxycarbonylamino-2-(3-methylsulphonylamino-phenyl)-acetylamino]-3-methoxy-3-cephem-4-carboxylate is obtained; Rf value ~ 0.21 (silica gel; toluene/acetone, 3:1); melting point, 127°–130° C (from ether/petroleum ether, 1:1); IR spectrum (in $CH_2Cl_2$): 3,430, 1,787, 1,720, 1,705, 1,492 and 1,160 $cm^{-1}$.

EXAMPLE 8

A solution of 709 mg (1 mmol) of diphenylmethyl 7β-[D-2-tert.-butoxycarbonylamino-2-(3-methylsulphonylamino-phenyl)-acetylamino]-3-hydroxy-3-cephem-4-carboxylate and 200 mg of 1-methyl-3-(4-methylphenyl)-triazene in 50 ml of benzene is boiled uner reflux for 2 hours. After cooling, the mixture is evporated under reduced pressure and the residue is purified over 30 times the amount of silica gel using toluene/ethyl acetate 3:1 as the eluant. Diphenylmethyl 7β-[D-2-tert.-butoxycarbonylamino-2-(3-methylsulphonylamino-phenyl)-acetylamino]-3methoxy-3-cephem-4-carboxylate is obtained; ultra-violet absorption spectrum (in ethanol): $\lambda_{max}$ = 265 nm ($\epsilon$= 6,900); infra-red absorption spectrum (in methylene chloride): characteristics bands at 3,420, 1,787, 1,720, 1,705, 1,492 and 1,160 $cm^{-1}$.

EXAMPLE 9

1.0 ml of dimethyl sulphate and 50 mg of anhydrous potassium carbonate are added to a mixture of 230 mg (0.325 mmol) of crude diphenylmethyl 7β-[D-α-tert.-butoxycarbonylamino-α-(3-methylsulphonylamino-phenyl)-acetylamino]-3-hydroxy-3-cephem-4-carboxylate and 20 ml of acetone and the reaction mixture is stirred for 16 hours at room temperature, under a nitrogen atmosphere. The reaction mixture is evaporated under reduced pressure, the residue is taken up in methylene chloride and the solution is washed with a saturated aqueous solution of sodium chloride, dried over sodium sulphate and evaporated under reduced pressure. The residue is purified by preparative layer chromatography (silica gel). The two zones which are visible under ultra-violet light (λ = 254 mμ) are isolated. Diphenylmethyl 7β-[D-2-tert.-butoxycarbonyl-amino-2-(3-methylsulphonylamino-phenyl)-acetylamino]-3-methoxy-2-cephem-4α-carboxylate, which has a Rf of ~ 0.28 (silica gel; system: toluene/acetone, 3:1) and diphenylmethyl 7β-[D-2-tert.-butoxycarbonylamino-2-(3-methylsulphonylamino-phenyl)-acetylamino]-3-methoxy-3-cephem-4-carboxylate, which has a Rf of ~ 0.22 (silica gel; system: toluene/acetone, 3:1) and a melting point of 127°–131° (from ether/petroleum ether, 1:1) are obtained.

EXAMPLE 10

0.12 ml of diisopropyl-ethylamine and 0.192 g of trimethyloxonium tetrafluoborate are added to a solution, which has been cooled to −10°, of 709 mg (1 mmol) of crude diphenylmethyl 7β-[D-2-tert.-butoxycarbonylamino-2-(3-methylsulphonyl-amino-phenyl)-acetylamino]-3-hydroxy-3-cephem-4-carboxylate in 30 ml of absolute methylene chloride and the mixture is stirred for 30 minutes at −10° under a nitrogen atmosphere; during this time the oxonium salt gradually dissolves. The reaction mixture is poured onto a mixture of ice and a saturated aqueous solution of sodium chloride; the aqueous mixture is extracted with twice 100 ml of methylene chloride and the organic phase is separated off, dried over sodium sulphate and evaporated under reduced pressure. The residue is purified by means of preparative layer chromatography (silica gel; system: toluene/ethylacetate. The zone which is visible under ultra-violet light (λ = 254 mμ) and which according to thin layer chromatography consists of a single compound is isolated and stirred with 20 ml of diethyl ether; after stirring for 16 hours, diphenylmethyl 7β-[D-2-tert.-butoxycarbonylamino-2-(3-methylsulphonylamino-phenyl)-acetylamino]-3-methoxy-3-cephem-4-carboxylate is obtained in a finely crystalline form; melting point 128°–131°; thin layer chromatogram (silica gel, developing with ninhydrin) Rf ~ 0.20 (toluene/acetone, 3:1).

EXAMPLE 11 a. 0.045 ml of diisopropyl-ethylamine and 0.03 ml of methyl trifluoromethanesulphonate are added to a solution of 115 mg (0.16 mmol) of crude diphenylmethyl 7β-[D-2-tert.-butoxycarbonylamino-2-(3-methylsulphonylamino-phenyl)-acetylamino]-3-hydroxy-3-cephem-4-carboxylate in 5 ml of methylene chloride and the mixture is stirred for 30 minutes under a nitrogen atmosphere and at room temperature. The reaction mixture is worked up by the process described in Example 10) and the product is purified by means of preparative layer chromatography, whereupon diphenylmethyl 7β-[D-2-tert.-butoxycarbonylamino-2-(3-methylsulphonylamino-phenyl)-acetylamino]-3-methoxy-3-cephem-4-carboxylate which has a melting point of 127°–129° is obtained.

b. Methyl fluorosulphonate can be used as the methylating agent, in place of methyl trifluoromethanesulphonate.

EXAMPLE 12 a. A solution of 223 mg (0.254 mmol) of diphenylmethyl 2-{4-(p-toluenesulphonylthio)-3-[D-2-tert.-butoxycarbonyl-amino-2-(3-methylsulphonylamino-phenyl)-acetylamino]-2-oxoazetidin-1-yl}-3-methoxycrotonate in 2 ml of dimethylformamide and 57 μl (0.38 mmol) of 1,5-diazabicyclo[5.4.0]undec-5-ene are stirred for 30 minutes at room temperature, ethyl acetate is then added and the mixture is washed with water and 2 N hydrochloric acid until it gives an acid reaction and with a saturated aqueous solution of sodium chloride until it gives a neutral reaction. The organic phase is dried over sodium sulphate and evaporated in vacuo. The residue is chromatographed on silica gel thick layer plates using 4:1 toluene/acetone as the running agent. This gives diphenylmethyl 7β-[D-2-tert.-butoxycarbonylamino-2-(3-methylsulphonylamino-phenyl)-acetylamino]-3-methoxy-2-cephem-4α-carboxylate;

thin layer chromatogram (silica gel; toluene/acetone, 3:1): Rf value ~ 0.28; IR spectrum (in methylene chloride): characteristic bands at 3,400, 1,780, 1,730, 1,700, 1,620, 1,490, 1,335 and 1,160 cm$^{-1}$; and diphenylmethyl 7β-[D-2-tert.-butoxycarbonylamino-2-(3-methylsulphonylamino-phenyl)acetylamino]-3-methoxy-3-cephem-4-carboxylate, which has a melting point of 127°–132° C (decomposition); thin layer chromatogram; Rf value: ~ 0.22 (silica gel; toluene/acetone, 3:1); UV spectrum (in ethanol) $\lambda_{max}$ = 265 nm ($\epsilon$ = 7,000); IR spectrum (in methylene chloride): 3,420 (broad), 1,785, 1,725, 1,705, 1,492, 1,340 and 1,160 cm$^{-1}$.

The starting material can be prepared as follows:

b. 16.5 ml (0.12 mol) of isobutyl chloroformate are added to a solution, which has been cooled to −15° C, of 41.33 g (0.12 mol) of D-2-tert.-butoxycarbonylamino-2-(3-methylsulphonylamino-phenyl)-acetic acid and 16.7 ml (0.12 mol) of triethylamine in 300 ml of tetrahydrofurane and the mixture is stirred for 30 minutes at −10° C. A solution of 21.6 (0.10 mmol) of 6-aminopenicillanic acid and 15.4 ml (0.11 mol) of triethylamine in 300 ml of 2:1 tetrahydrofurane/water is then added. The reaction mixture is stirred for 1 hour at 0° C and for 2 hours at room temperature, during which time the pH value is kept constant at about 6.9 by adding triethylamine. The pH of the reaction mixture is adjusted to 2.0 with phosphoric acid, at 5° C, and the mixture is saturated with sodium chloride and extracted with three times 500 ml of ethyl acetate and the organic phase is washed with a saturated aqueous solution of sodium chloride, dried over sodium sulphate and evaporated. The crude 6β-[D-2-tert.-butoxycarbonylamino-2-(3-methylsulphonylaminophenyl)-acetylamino]-2,2-dimethyl-penam-4α-carboxylic acid which is obtained in the form of a pale yellow foam has a Rf value, in the thin layer chromatogram, of 0.60. (Silica gel; ethyl acetate/n-butanol/pyridine/acetic acid/water, 42:21:21:6:10).

c. 21.6 ml (0.25 mol) of 30% strength hydrogen peroxide are added to a solution of 67.84 g of crude 6β-[D-2-tert.-butoxycarbonylamino-2-(3-methylsulphonylamino-phenyl)-acetylamino]-2,2-dimethyl-penam-4α-carboxylic acid in 100 ml of glacial acetic acid in the course of 10 minutes and the mixture is stirred for 2.5 hours at room temperature. The reaction mixture is then poured into 2 litres of ice water and 6β-[D-α-tert.-butoxycarbonylamino-α-(3-methylsulphonylamino-phenyl)-acetylamino]-2,2-dimethyl-penam-4α-carboxylic acid 1-oxide, which is obtained in the form of a voluminous precipitate, is filtered off, washed well with water and dried in vacuo. Further amounts of crude 6β-[D-2-tert.-butoxycarbonylamino-2-(3-methylsulphonylamino-phenyl)-acetylamino]-2,2-dimethyl-penam-4α-carboxylic acid 1-oxide can be obtained by extracting the filtrate with ethyl acetate. Thin layer chromatogram (silica gel: ethylacetate/n-butanol/pyridine/-acetic acid/water 42:21:21:6:10) Rf value ~ 0.30.

d. A solution of 32.9 g (0.18 mol) of diphenyldiazomethane in 130 ml of dioxane is added to a mixture of 87 g (approximately 0.12 mol) of crude 6β-[D-2-tert.-butoxycarbonylamino-2-(3-methylsulphonylamino-phenyl)-acetylamino]-2,2-dimethyl-phenam-4α-carboxylic acid 1-oxide in 380 ml of dioxane and the mixture is stirred for 2.5 hours at room temperature. After adding 5 ml of glacial acetic acid, the mixture is evaporated in vacuo. The residue is digested with petroleum ether, the petroleum ether extract is discarded and the residue, that is to say the 1-oxide of diphenylmethyl 6β-[D-2-tert.-butoxycarbonylamino-2-(3-methylsulphonylamino-phenyl)acetylamino]-2,2-dimethyl-penam-4α-carboxylate, is isolated as an amorphous powder; IR spectrum (methylene chloride): characteristic bands at 3,450, 3,430, 1,798, 1,750, 1,725, 1,697, 1,510, 1390 and 1,155 cm$^{-1}$; thin layer chromatogram: Rf value ~ 0.22, (silica gel; toluene/ethyl acetate, 3:1).

e. A mixture of 12.8 g (17.7 mmols) of the 1-oxide of diphenylmethyl 6β-[D-2-tert.-butoxycarbonylamino-2-(3-methylsulphonylamino-phenyl)-acetylamino]-2,2-dimethyl-penam-4α-carboxylate and 3.26 g (19.5 mmols) of mercaptobenzthiazole in 170 ml of toluene is boiled for 3 hours in a reflux apparatus which has a water separator and is then evaporated. The residue is chromatographed over silica gel using 3:1 toluene/ethyl acetate as the eluant and gives amorphous diphenylmethyl 2-{4-(benzthiazol-2-yldithio)-3-[2-tert.-butoxycarbonylamino-2-(3-methylsulphonylamino-phenyl)-acetylamino]-2-oxoazetidin-1-yl}-3-methylenebutyrate; thin layer chromatogram: Rf value ~ 0.38 (silica gel; toluene/ethyl acetate, 3:1).

f. 0.868 g (3.46 mmols) of silver toluenesulphinate is added, at 0° C, to a solution of 2.62 g (3.0 mmols) of diphenylmethyl 2-{4-(benzthiazol-2-yldithio)-3-[2-tert.-butoxycarbonylamino-2-(3-methylsulphonylamino-phenyl)-acetylamino]-2-oxoazetidin-1-yl}-3-methylenebutyrate in 30 ml of 9:1 acetone/water and the mixture is stirred for 1 hour in an ice bath. The precipitate which has separated out is filtered off. The filtrate is taken up in toluene and extracted by shaking with a saturated aqueous solution of sodium chloride. The organic phase is dried over sodium sulphate and, after evaporation, gives amorphous diphenylmethyl 2-{4-(p-toluenesulphonylthio)-3-[2-tert.-butoxycarbonylamino-2-(3-methylsulphonylamino-phenyl)-acetylamino]-2-oxoazetidin-1-yl}-3-methylene-butyrate; thin layer chromatogram: Rf value ~ 0.33 (silica gel; toluene/ethyl acetate, 3:1); IR spectrum (methylene chloride): characteristic bands at 3,440, 3,430, 1,785, 1,752, 1,722, 1,620, 1,510, 1,390 and 1,160 cm$^{-1}$.

g. A stream of ozone/oxygen (0.5 mmol of ozone per minute) is passed into a solution, which has been cooled to −70° C, of 2.59 g (3.0 mmols) of diphenylmethyl 2-{4-p-toluenesulphonylthio)-3-[2-tert.-butoxycarbonylamino-2-(3-methylsulphonylamnio-phenyl)-acetylamino]-2-oxoazetidin-1-yl}-3-methylene-butyrate in 230 ml of methylene chloride for 7 minutes. After adding 1 ml of dimethyl sulphide, the solution is stirred for a further 1 hour without cooling and then evaporated in vacuo. The residue, that is to say diphenylmethyl 2-{4-(p-toluenesulphonylthio)-3-[2-tert.-butoxycarbonylamino-2-(3-methylsulphonylamino-phenyl)-acetylamino]-2-oxoazetidin-1-yl}-3-hydroxy-crotonate, is obtained as an amorphous powder; IR spectrum (methylene chloride): characteristic bands at 3,430, 1,785, 1,720, 1,680, 1,665 (shoulder), 1,620, 1,385 and 1,160 cm$^{-1}$; thin layer chromatogram: Rf value ~ 0.56 (silica gel; toluene/ethyl acetate, 1:1).

h. A solution of 6.06 g (0.07 mmol) of diphenylmethyl 2-{4-(p-toluenesulphonylthio)-3-[2-tert.-butoxycarbonylamino-2-(3-methylsulphonylamino-phenyl)-acetylamino]-2-oxoazetidin-1-yl}-3-hydroxy-crotonate in 20 ml of 1:1 methylene chloride/methanol is stirred with an excess of an ethereal solution of diazomethane for 15 minutes at 0° C and the mixture is then evaporated in vacuo. Preparative layer chromatography of the residue on silica gel using 1:1 toluene/ethyl acetate as the running agent and elution of the zone visible in UV light gives diphenylmethyl 2-{4-(p-toluenesulphonylthio)-3-[2-tert.-butoxycarbonylamino-2-3-methylsulphonylamino-phenyl-acetylamino]-2-oxoazetidin-1-yl}-3-methoxy-crotonate; thin layer chromatogram: Rf value ~ 0.32 (silica gel; toluene/ethyl acetate, 1:1.

EXAMPLE 13

A solution of 0.20 g of 3-chloro-perbenzoic acid in 5 ml of methylene chloride is added to a solution, which has been cooled to 0° C, of 0.723 g (1 mmol) of diphenylmethyl 7$\beta$-[D-2-tert.-butoxycarbonylamino-2-(3-methylsulphonylaminophenyl)-acetylamino]-3-methoxy-2-cephem-4$\alpha$-carboxylate in 25 ml of methylene chloride. The mixture is stirred for 30 minutes at 0° C, 50 ml of methylene chloride are added and the mixture is washed successively with 25 ml of a saturated aqueous solution of sodium bicarbonate and 25 ml of a saturated aqueous solution of sodium chloride. The organic phase is dried over sodium sulphate and evaporated under reduced pressure. The crude product is chromatographed over 30 times the amount of silica gel, using 4:1 toluene/acetone as the eluant, and the 1-oxide of diphenylmethyl 7$\beta$-[D-2-tert.-butoxycarbonylamino-2-(3-methylsulphonylamino-phenyl)-acetylamino]-3-methoxy-3-cephem-4-carboxylate is thus obtained in an amorphous form; thin layer chromatogram: Rf ~ 0.15 (silica gel; toluene/acetone, 3:1; developing with iodine vapour); infra-red absorption spectrum (in methylene chloride): characteristic bands at 3,420, 1,780, 1,700, 1,490, 1,333, 1,160 and 1,050 cm$^{-1}$.

EXAMPLE 14

2.80 g of phosphorus trichloride are added to a solution, which has been cooled to $-10°$ C, of 1.48 g (2 mmols) of the 1-oxide of diphenylmethyl 7$\beta$-[D-2-tert.-butoxycarbonylamino-2-(3-methylsulphonylaminophenyl)-acetylamino]-3-methoxy-3-cephem-4carboxylate in 30 ml of dimethylformamide, with the exclusion of air. After it has been left to stand for 15 minutes, the reaction mixture is poured out onto a mixture of ice and an aqueous solution of dipotassium hydrogen phosphate; the aqueous mixture is extracted with twice 100 ml of ethyl acetate. The organic extract is washed with a saturated aqueous solution of sodium chloride, dried over sodium sulphate and evaporated. The residue is chromatographed on silica gel; elution with 3:1 toluene/actone gives amorphous diphenylmethyl 7$\beta$-[D-2-tert.-butoxy-carbonylamino-2-(3-methylsulphonylamino-phenyl)-acetylamino[-3-methoxy-3-cephem-4-carboxylate, which according to thin layer chromatography is the pure substance, Rf ~ 0.22 (silica gel; toluene/acetone, 3:1; developing with iodine vapour); ultra-violet absorption spectrum (in ethanol): $\lambda_{max}$ = 265 nm ($\epsilon$ = 6,950); infra-red absorption spectrum (in methylene chloride): characteristic bands at 3,420, 1,780, 1,725, 1,700, 1,335 and 1,160 cm$^{-1}$.

EXAMPLE 15 a. 1.4 ml of bis-(trimethylsilyl)-acetamide are added to a suspension of 2.4 g (5 mmols) of 7$\beta$-[D-2-tert.-butoxy-carbonylamino-2-(3-aminophenyl)-acetylamino[-3-methoxy-3-cephem-4-carboxylic acid in 20 ml of absolute methylene chloride, under nitrogen and with the exclusion of moisture, and the mixture is stirred for 45 minutes at room temperature. The clear, pale yellow solution is cooled to 0° C and, whilst stirring, 1.2 ml of absolute pyridine and then 0.63 g (5.5 mmols) of methylsulphonyl chloride dissolved in 10 ml of absolute methylene chloride are added. After 1 hour at 0° C and 4 hours at room temperature, 2 ml of methanol are added to the reaction mixture and the latter is freed from solvent in a rotary evaporator. The oily residue is taken up in 20 ml of water, the pH is adjusted to 2.0 with 2 N hydrochloric acid and the aqueous phase is extracted with twice 50 ml of ethyl acetate. The combined organic phases are dried (MgSO$_4$) and concentrated in a rotary evaporator. The residue is purified over silica gel using a 1:1 mixture of methylene chloride and ethyl acetate as the eluant. This gives 7$\beta$-[D-2-tert.-butoxycarbonylamino-2-(3-methylsulphonylaminophenyl)-acetylamino[-3-methoxy-3-cephem-4-carboxylic acid, which according to thin layer chromatography is a single compound and which, when recrystallised from 1:3 methylene chloride/diethyl ether, melts at 140° with decomposition. Thin layer chromatogram (silica gel; identification with ninhydrin): Rf~0.63 (system: sec.butanol/acetic acid/water, 67:10:23).

The starting material can be prepared as follows:

b. 3.8 ml of bis-(trimethylsilyl)-acetamide and added to a suspension of 3.11 g (13.5 mmols) of finely powdered 7$\beta$-amino-3-methoxy-3-cephem-4-carboxylic acid in 60 ml of absolute methylene chloride, under an argon atmosphere and at room temperature, (the addition is effected in the course of about 10 minutes) and the mixture is stirred for 45 minutes.

1.97 ml of isobutyl chloroformate are added to a solution, which has been cooled to $-15°$, of 4.44 g (15 mmols) of D-2-tert.-butoxycarbonylamino-2-(3-nitrophenyl)-acetic acid and 1.67 ml of 4-methyl-morpholine in 90 ml of absolute acetonitrile, under an argon atmosphere, and the mixture is allowed to react for a further 25 minutes. The silylated starting material described above is added dropwise, at $-15°$, to the mixed anhydride which is thus obtainable and the reaction mixture is stirred for 2 hours at 0° and for 30 minutes at room temperature. The solvent is then removed in a rotary evaporator and the residue is taken up in 200 ml of ethyl acetate and washed three times with a saturated aqueous solution of sodium chloride. The aqueous phases are again extracted with ethyl acetate. The combined organic solutions are dried over magnesium sulphate and freed from solvent under reduced pressure. The residue is purified over silica gel using a 1:1 mixture of methylene chloride and ethyl acetate as the eluant. This gives 7$\beta$-[D-2-tert.-butoxycarbonylamino-2-(3-nitrophenyl)-acetylamino]-3-methoxy-3-cephem-4-carboxylic acid, which according to thin layer chromatography is a single compound, as an amorphous product; thin layer chromatogram (silica gel; identification with ninhydrin): Rf~0.52 (system: sec.-butanol/acetic acid/water, 67:10:23), infra-red absorption spectrum (in methylene chloride): characteristic bands at 3,400, 1,785, 1,710, 1,535 and 1,355 cm$^{-1}$.

c. 1.17 g (2 mmols) of 7$\beta$-[D-2-tert.-butoxycarbonylamino-2-(3-nitrophenyl)-acetylamino[-3-methoxy-3-cephen-4-carboxylic acid, dissolved in 30 ml of ethyl acetate, are hydrogenated at room temperature and under normal pressure in the presence of 200 mg of 5% strength palladium-on-charcoal until 3 equivalents of hydrogen have been taken up. The catalyst is filtered off and washed with a little ethyl acetate. The solvent is stripped off under reduced pressure. The resulting crude product, that is to say 7$\beta$-[D-2-tert.-butoxy-carbonylamino-2-(3-aminophenyl)acetylamino]-3- methoxy-3-cephem-4-carboxylic acid, is used direct for the sulphonylation.

EXAMPLE 16 a. 482 mg (1 mmole) of 7β-[D-2-azido-2-(3-methylsulphonylamino-phenyl)-acetylamino]-3-methoxy-3-cephem-4-carboxylic acid, dissolved in 32 ml of 3:1 methanol/chloroform, are hydrogenated in the presence of 120 mg of platinum oxide at room temperature and under normal pressure (reaction time: 2 hours). The solution is diluted with 5 ml of water and the pH is adjusted to 2 with 1 ml of 1 N hydrochloric acid. After filtering, the pH of the aqueous phase is adjusted to 5.2 with a 20% strength solution of triethylamine in methanol. The solution is concentrated to about half its volume, 12 ml of acetone are added and the mixture is left to stand for 16 hours at about −18°. The precipitate which has formed is filtered off, washed with acetone and diethyl ether and dried. In this way 7β-[D-2-amino-2-(3-methylsulphonylamino-phenyl)-acetylamino]-3-methoxy-3-cephem-4-carboxylic acid is obtained in the form of the inner salt, as the monohydrate, which decomposes above 170°; thin layer chromatogram (silica gel; identification with ninhydrin): Rf~0.20 (system: sec.-butanol/acetic acid/water, 67:10:23); ultra-violet absorption spectrum (in 0.1 N aqueous) hydrochloric acid): $\lambda_{max}$ = 272 nm ($\epsilon$ = 7200).

The starting material can be prepared as follows:

b. 0.75 ml of bis-(trimethylsilyl)-acetamide is added to a suspension of 0.622 g (2.7 mmols) of finely powdered 7β-amino-3-methoxy-3-cephem-4-carboxylic acid in 12 ml of absolute methylene chloride, under an argon atmosphere and at room temperature (the addition is effected in the course of about 10 minutes) and the mixture is stirred for 45 minutes.

0.4 ml of isobutyl chloroformate is added to a solution, which has been cooled to −15°, of 0.81 g (3.0 mmols) of D-2-azido-2-(3-methylsulphonylamino-phenyl)-acetic acid and 0.33 ml of 4-methyl-morpholine in 18 ml of absolute acetonitrile, under an argon atmosphere, and the mixture is allowed to react for a further 25 minutes. The silylated starting material described above is added dropwise, at −15°, to the mixed anhydride which is thus obtainable and the reaction mixture is stirred for 2 hours at 0° and for 30 minutes at room temperature. The solvent is then removed in a rotary evaporator and the residue is taken up in 400 ml of ethyl acetate and washed three times with a saturated aqueous solution of sodium chloride. The aqueous phases are again extracted with ethyl acetate. The combined organic solutions are dried over magnesium sulphate and freed from solvent under reduced pressure. The residue is purified over silica gel using a 1:1 mixture of methylene chloride and ethyl acetate as the eluant. 7β-[D-2-Azido-2-(3-methylsulphonylamino-phenyl)-acetylamino]-3-methoxy-3-cephem-4-carboxylic acid, which according to thin layer chromatography is a single compound, is obtained as an amorphous product, which is employed direct in the next synthesis step.

EXAMPLE 17

A mixture of 1.45 g (2 mmols) of diphenylmethyl 7β-[D-2-tert.-butoxycarbonylamino-2-(3-methylsulphonylamino-phenyl)-acetylamino]-3-methoxy-2-cephem-4α-carboxylate and 0.2 ml of diisopropyl ethylamine in 30 ml of methyl chloride is left to stand for 6 hours at room temperature. After removing the solvent, the resulting mixture of starting material and diphenylmethyl 7β-[D-2-tert.-butoxycarbonylamino-2-(3-methylsulphonylamino-phenyl)acetylamino-3-methoxy-3-cephem-4-carboxylate is chromatographed over silica gel using 3:1 toluene/acetone as the eluant. Diphenylmethyl 7β-[D-2-tert.-butoxycarbonylamino-2-(3-methylsulphonylamino-phenyl)-acetylamino]-3-methoxy-3-cephem-4-carboxylate is isolated therefrom in a crystalline form; melting point 128°–130°; thin layer chromatogram (silica gel, developing with iodine vapour): Rf~0.22 (toluene/acetone, 3:1).

EXAMPLE 18

12.5 mmols of solid phosphorus pentachloride are added, at −20°, to a solution of 10 mmols of diphenylmethyl 7β-(2-phenoxyacetylamino)-3-methoxy-3-cephem-4-carboxylate and 25 mmols of N,N-dimethylaniline in 50 ml of absolute methylene chloride and the mixture is then stirred for 30 minutes at −20°. A cold mixture of 0.2 mol of methanol and 12 mmols of N,N-dimethylaniline is then added at this temperature and the mixture is then stirred for 2 hours at 0°. 60 mmols of N-methylmorpholine and a solution of the mixed anhydride prepared by stirring a mixture of 15 mmols of D-2-(tert.-butoxycarbonylamino)-2-(3-methylsulphonylamino-phenyl)-acetic acid, 14 mmols of isobutyl chloroformate and 16 mmols of N-methylmorpholine in 50 ml of methylene chloride for 30 minutes at 0° are added at 0° and the mixture is stirred for 1 hour at 0°. 100 ml of $H_2O$ are added, the mixture is shaken, the phases are separated and the organic phase is washed with a phosphate buffer with a pH of 2 and with a phosphate buffer with a pH of 6. Drying the extract with sodium sulphate and evaporating gives diphenylmethyl 7β-[D-2-tert.-butoxycarbonylamino-2-(3-methylsulphonylamino-phenyl)-acetylamino]-3-methoxy-3-cephem-4-carboxylate, which is dissolved in 20 ml of trifluoroacetic acid and 1 ml of anisole. After standing for 10 minutes at room temperature, the solution is evaporated, the residue is taken up in methanol and 7β-[D-2-amino-2-(3-methylsulphonylamino-phenyl)-acetylamino]-3-methoxy-3-cephem-4-carboxylic acid is precipitated by carefully adding diethylamine (until the isoelectric point is reached).

EXAMPLE 19 a. *Pseudomonas melanogenum ATCC* 17,808 is cultured, as a submersed culture, for 55 hours at 28° in a medium containing 0.7% of acetone, 0.5% of meat extract, 0.5% of yeast extract, 0.5% of sodium L-glutamate and 0.3% of sodium chloride. The cells are centrifuged off, washed with 0.8 percent strength sodium chloride solution and suspended in a 0.1 normal acetate buffer which has a pH of 6.5. 1 g of 7β-amino-3-methoxy-3-cephem-4-carboxylic acid and 3 g of the hydrochloride of methyl D-2-(3-methylsulphonylamino-phenyl)-glycinate are added to 100 ml of this suspension (containing about 6 g of moist cells) and the mixture is stirred for 2 hours at 35°. The mixture is centrifuged and the clarified filtrate is introduced into a column of Amberlite XAD-2. After washing the column with water, 7β-[D-2-amino-2-(3-methylsulphonylamino-phenyl)-acetylamino]-3-methoxy-3-cephem-4-carboxylic acid is eluted with increasing proportions of methanol in water.

b. The hydrochloride of methyl D-2-(3-methylsulphonyl-amino-phenyl)-glycinate is obtained from D-2-(3-methyl-sulphonylamino-phenyl)-glycine by esterification with methanol in the presence of dry hydrogen chloride.

The protective groups can be split off from the resulting compounds as follows:

EXAMPLE 20 a. A mixture of 0.557 g of 7β-[D-2-tert.-butoxycarbonyl-amino)-2-(3-methylsulphonylamino-phenyl)-acetylamino]-3-methoxy-3-cephem-4-carboxylic acid, 2.5 ml of pre-cooled trifluoroacetic acid and 2.5 ml of pre-cooled trifluoroacetic acid and 2.5 ml of methylene chloride is stirred for 30 minutes at 0° under an argon atmosphere and 25 ml of a 1:1 mixture of petroleum ether and diethyl ether is then added at 0°. The beige precipitate is filtered off, washed with a little diethyl ether and dried under reduced pressure. The trifluoroacetic acid salt of 7β-[D-2-amino-2-(3-methylsulphonylamino-phenyl)-acetylamino]-3-methoxy-3-cephem-4-carboxylic acid, which is thus obtained, is dissolved in 5 ml of water, the solution is extracted with twice 3 ml of ethyl acetate and the pH value of the acid aqueous phase (pH 1.8) is adjusted to 5.2 by dropwise addition of a 2 N aqueous solution of sodium hydroxide. The solution is concentrated to about half its volume, 12 ml of acetone are added and the mixture is left to stand for 16 hours at about −18°. The precipitate which has formed is filtered off, washed with acetone and diethyl ether and dried. In this way 7β-[D-2-amino-2-(3-methylsulphonylamino-phenyl)-acetylamino]-3-methoxy-3-cephem-4-carboxylic acid is obtained in the form of the inner salt, as the monohydrate, which decomposes above 170°; thin layer chromatogram (silica gel; identification with ninhydrin): Rf∼0.22 (system: sec.-butanol/acetic acid/water, 67:10:23); ultra-violet absorption spectrum (in 0.1 N aqueous hydrochloric acid): $\lambda_{max} = 272$ nm ($\epsilon = 7000$).

The same compound can also be obtained as follows:

ai. 40 ml of pre-cooled trifluoroacetic acid are added to a solution, which has been cooled to 0°, of 8.0 g (14.4 mmols) of 7β-[D-2-tert.-butoxycarbonylamino-2-(3-methylsulphonyl-amino-phenyl)-acetylamino]-3-methoxy-3-cephem-4-carboxylic acid in 40 ml of absolute methylene chloride, the mixture is stirred for 25 minutes at 0° under an argon atmosphere and 500 ml of a 1:1 mixture of petroleum ether and diethyl ether are then added at 0°. The beige precipitate is filtered off, washed with a little diethyl ether and dried under reduced pressure. The trifluoroacetic acid salt of 7β-[D-2-amino-2-(methylsulphonylamino-phenyl)-acetylamino]-3-methoxy-3-cephem-4-carboxylic acid, which is thus obtained, is dissolved in 70 ml of ice water and the solution is extracted with three times 30 ml of ethyl acetate. The pH value of the acid aqueous phase (pH ∼2.0) is adjusted to 5.2 by the dropwise addition of a 20% strength solution of triethylamine in methanol and 160 ml of isopropanol are added at 0°. The precipitate which has formed is recrystallised from 2:1 isopropanol/water, filtered off, washed with a little isopropanol and dried. Since the crystals still contain a small amount of organid solvent, even after drying, they are digested for a further ½ hour in 50% strength aqueous solution at 40°, the solution is cooled to 0°, filtered and the product is again dried at room temperature under a high vacuum. In this way 7β-[D-2-amino-2-(3-methylsulphonyl-amino-phenyl)-acetylamino]-3-methoxy-3-cephem-4-carboxylic acid is obtained in the form the inner salt which is also in the form of a monohydrate; melting point above 174° (with decomposition).

aii. A solution of 300 mg (0.54 mmol) of 7β-[D-2-tert.-butoxycarbonylamino-2-(3-methylsulphonylamino-phenyl)-acetyl-amino]-3-methoxy-3-cephem-4-carboxylic acid in 3 ml of formic acid is stirred for 3 hours at room temperature under argon and then cooled to 0° and subsequently 30 ml of 1:1 diethyl ether/petroleum ether are added. The formic acid salt of 7β-[D-2-amino-2-(3-methylsulphonylamino-phenyl)-acetylamino]-3-methoxy-3-cephem-4-carboxylic acid, which has precipitated, is dissolved in 3 ml of ice water and the solution is extracted with three times 1.5 ml of ethyl acetate and freed from water and from excess formic acid in a rotary evaporator. The residue is taken up in water twice more, using 3 ml in each case, and the solution is concentrated to dryness and, from the residue, the monohydrate of 7β-[D-2-amino-2-(3-methylsulphonylamino-phenyl)-acetylamino]-3-methoxy-4-carboxylic acid can be isolated direct in the form of pale yellow crystals which have a melting point of 173°–175° (decomposition); thin layer chromatogram (silica gel; developing with ninhydrin): Rf∼0.21 (system: sec.-butanol/acetic acid/water, 67:10:23); UV spectrum (in 0.1 N aqueous hydrochloric acid): $\lambda_{max} = 272$ nm ($\epsilon = 7,100$).

aiii. A solution of 2.2 g of 7β-[D-2-tert.-butoxycarbonyl-amino-2-(3-methylsulphonylamino-phenyl)-acetylamino]-3-methoxy-3-cephem-4-carboxylic acid in 22 ml of 99% strength formic acid is left to stand for 1½ hours at 23° and is then evaporated in vacuo. The resulting resin is digested successively with 25 ml of ether, 25 ml of acetonitrile and 25 ml of 95:5 acetonitrile/H₂O. 7β-[D-2-Amino-2-(3-methylsulphonylamino-phenyl)-acetylamino]-3-methoxy-3-cephem-4-carboxylic acid is obtained as a pale beige powder. After recrystallisation from 1:2 water/isopropanol, the monohydrate has the following characteristics: $[\alpha]_D^{20} = +143° \pm 1°$ ($c = 1$, 0.1 N HCl), UV absorption in 0.1 H HCl: $\lambda_{max} = 272$ nm ($\epsilon = 7,300$).

EXAMPLE 21 a. In a manner analogous to Example 20a, the amino group in 7β-[D-2-tert.-butoxycarbonylamino-2-(3-methylsulphonylamino-phenyl)-acetylamino]-3-chloro-3-cephem-4-carboxylic acid can be liberated by reaction with trifluoroacetic acid and the resulting trifluoroacetic acid salt of 4β-[D-2-amino-2-(3-methylsulphonylamino-phenyl)-acetylamino]-3-chloro-3-cephem-4-carboxylic acid can be converted, by treating it with an aqueous solution of sodium hydroxide until the isoelectric point is reached, to the inner salt of 7β-[D-2-amino-2-(3-methylsulphonylamino-phenyl)-acetylamino]-3-chloro-3-cephem-4-carboxylic acid.

ai. In a manner analogous to Example 20 (ai), the amino group in 7β-[D-2-tert.-butoxycarbonylamino-2-(3-methyl-sulphonylamino-phenyl)-acetylamino]-3-chloro-3-cephem-4-carboxylic acid can be liberated by reaction with trifluoroacetic acid and the resulting trifluoroacetic acid salt of 7β-[D-2-amino-2-(3-methylsulphonylamino-phenyl)-acetylamino]-3-chloro-3-cephem-4-carboxylic acid can be converted, by treating it with a 20% strength solution of triethylamine in methanol until the isoelectric point is reached, to the inner salt of 7β-[D-2-amino-2-(3-methylsulphonylamino-phenyl)-acetylamino]-3-chloro-3-cephem-4-carboxylic acid; melting point above 165° (decomposition); thin layer chromatogram (silica gel, developing with ninhydrin); Rf ∼ 0.17 (system: sec.-butanol/acetic acid/water, 67:10:23); UV spectrum (0.1 N hydrochloric acid): $\lambda_{max}$ = 267 nm ($\epsilon$ = 7,600).

aii. In a manner analogous to Example 20 (aiii), the amino group in 7β-[D-2-tert.-butoxycarbonylamino-2-(3-methyl-sulphonylamino-phenyl)-acetylamino]-3-chloro-3-cephem-4-carboxylic acid can be liberated by reaction with formic acid. 7β-[D-2-Amino-2-(3-methylsulphonylamino-phenyl)-acetylamino]-3-chloro-cephem-4-carboxylic acid is obtained as fine crystals which have the same physical characteristics as those indicated under (ai).

EXAMPLE 22

A solution of 2.18 g (3 mmols) of diphenylmethyl 7β-[D-2-tert.-butoxycarbonylamino-2-(3-methylsulphonylamino-phenyl)acetylamino]-3-chloro-3-cephem-4-carboxylate, 1.8 ml of anisole and 9.6 ml of trifluoroacetic acid in 20 ml of methylene chloride is stirred for 30 minutes at 0° and 200 ml of 1:1 ether/petroleum ether are then added. The trifluoroacetic acid salt is dissolved in 10 ml of ice water and the solution is extracted with twice 4 ml of ethyl acetate. The pH of the aqueous phase is adjusted to 5.0 with a 20% strength solution of triethylamine in methanol and after 24 ml of isopropanol have been added a colourless precipitate forms. After filtering, washing with a little isopropanol and drying under reduced pressure, colourless crystals of 7β-[D-2-amino-2-(3-methylsulphonylamino-phenyl)-acetylamino]-3-chloro-3-cephem-4-carboxylic acid are obtained; melting point above 165° (decomposition); thin layer chromatogram (silica gel, developing with ninhydrin): Rf ~ 0.17 (system: sec.-butanol/acetic acid/water, 67:10:23); IR spectrum (in Nujol): characteristic bands at 3,500, 3,220, 1,780, 1,685, 1,340 and 1,155 cm$^{-1}$.

EXAMPLE 23 a. In a manner analogous to Example 22 it is possible, by treating 1.08 g (1.5 mmols) of diphenylmethyl 7β-[D-2-tert.-butoxycarbonylamino-2-(3-methylsulphonylamino-phenyl)-acetylamino]-3-methoxy-3-cephem-4-carboxylate with 4.5 ml of trifluoroacetic acid and 0.8 ml of anisole in 10 ml of methylene chloride, to liberate the amino group and the protected 4-carboxyl group and to convert the resulting trifluoroacetic acid salt, by treating it with a 20% strength solution of triethylamine in methanol until the isoelectric point is reached, into the inner salt of 7β-[D-2-amino-2-(3-methylsulphonylamino-phenyl)acetylamino]-3-methoxy-3-cephem-4-carboxylic acid; melting point above 172° (decomposition).

ai. A mixture of 10.12 g (14 mmols) of diphenylmethyl 7β-[D-2-tert.-butoxycarbonylamino-2-3-methylsulphonylamino-phenyl)-acetylamino]-3-methoxy-3-cephem-4-carboxylate, 8.6 ml of anisole and 145 ml of trifluoroacetic acid is stirred for 15 minutes at 0° C, 400 ml of pre-cooled toluene are then added and the mixture is evaporated under reduced pressure. The residue is dried under a high vacuum and digested with diethyl ether and the product is filtered off. In this way the trifluoroacetate of 7β-[D-2-amino-2-(3-methylsulphonyl-amino-phenyl)-acetylamino]-3-methoxy-3-cephem-4-carboxylic acid is obtained in a pulverulent form and this is dissolved in 70 ml of water. The solution is washed three times 25 ml of ethyl acetate and the pH value is adjusted to about 5.6 with a 20% strength solution of triethylamine in methanol and, after 160 ml of isopropanol have been added, a colourless precipitate forms. The mixture is stirred for 1 hour in an ice bath. The colourless precipitate is filtered off, washed with isopropanol and diethyl ether and dried under reduced pressure. Since the crystals still contain a little isopropanol and diethyl ether, even after drying, they are digested for a further ½ hour in 50% strength aqueous solution at 40° C, the solution is cooled to 0° and filtered and the product is again dried. In this way 7β-[D-2-amino-2-(3-methylsulphonylamino-phenyl)-acetamido]-3-methoxy-3-cephem-4-carboxylic acid, as an inner salt, which is also in the form of a monohydrate, is obtained in the form of a microcrystalline powder; melting point above 175° C (with decomposition); $[\alpha]_D^{20}$ = + 144° ($c$ = 1.035 in 0.1 N hydrochloric acid); thin layer chromatogram (silica gel; developing with ninhydrin): Rf ~ 0.19 (system: sec.-butanol/acetic acid/water, 67:10:23); ultra-violet absorption spectrum (in 0.1 N aqueous hydrochloric acid): $\lambda_{max}$ = 272 nm ($\epsilon$ = 7,300); infra-red absorption spectrum (in mineral oil): characteristic bands at, inter alia, 3,500, 3,180, 1,760, 1,692, 1,608, 1,150 and 978 cm$^{-1}$.

EXAMPLE 24

A suspension of 4.75 g of 7β-[D-2-amino-2-(3-methylsulphonylamino-phenyl)-acetylamino]-3-methoxy-3-cephem-4-carboxylic acid in 50 ml of water and 2 ml of alcohol is slowly brought into solution, at a pH value of less than 7.6, using a total of about 5 ml of 2 N sodium hydroxide solution, whilst stirring and regulating the pH. On lyophilisation, the solution, which has been freed from a small amount of residual solids by filtration, gives 4.9 g of sodium 7β-[D-2-amino-2-(3-methylsulphonylamino-phenyl)-acetylamino]-3-methoxy-3-cephem-4-carboxylate.

EXAMPLE 25

Dry ampoules or phials containing 0.5 g of the inner salt of 7β-[D-2-amino-2-(3-methylsulphonylamino-phenyl)-acetylamino]-3-methoxy-3-cephem-4-carboxylic acid are manufactured as follows:

| Composition (for 1 ampoule or phial) | |
|---|---|
| Inner salt of 7β-[D-2-amino-2-(3-methylsulphonyl-amino-phenyl)-acetylamino]-3-methoxy-3-cephem-carboxylic acid | 0.5 g |
| Mannitol | 0.05 g |

A sterile aqueous solution of the inner salt of 7β-[D-2-amino-2-(3-methylsulphonylamino-phenyl)-acetylamino]-3-methoxy-3-cephem-4-carboxylic acid and of mannitol is subjected to freeze-drying under aseptic conditions in 5 ml ampoules or 5 ml phials and the ampoules or phials are sealed and checked.

EXAMPLE 26

Capsules containing 0.25 g of the inner salt of 7β-[D-2-amino-2-(3-methylsulphonylamino-phenyl)-acetylamino]-3-methoxy-3-cephem-4-carboxylic acid are manufactured as follows:

| Composition (for 1,000 capsules): | |
|---|---|
| Inner salt of 7β-[D-2-amino-2-(3-methylsulphonyl-amino-phenyl)-acetylamino]-3-methoxy-3-cephem-4-carboxylic acid | 250,000 g |
| maize starch | 50,000 g |
| polyvinylpyrrolidone | 15,000 g |
| magnesium stearate | 5,000 g |

-continued

| Composition (for 1,000 capsules): | |
|---|---|
| ethanol | q.s. |

The inner salt of 7β-[D-2-amino-2-(3-methylsulphonylamino-phenyl)-acetylamino]-3-methoxy-3-cephem-4-carboxylic acid and the maize starch are mixed and the mixture is moistened with a solution of the polyvinylpyrrolidone in 50 g of ethanol. The moist mass is pressed through a sieve with a mesh width of 3 mm and dried at 45°. The dry granules are forced through a sieve with a mesh width of 1 mm and mixed with 5 g of magnesium stearate. The mixture is filled, in portions of 0.320 g, into size 0 push-fit capsules.

What is claimed is:

1. A 7β-[D-2-amino-2-(lower alkylsulphonylamino-phenyl)-acetylamino]-3-R-3-cephem-4-carboxylic acid (I), in which R denotes lower alkoxy or halogen with an atomic number of up to 35, or a pharmaceutically acceptable salt thereof.

2. A compound according to claim 1, in which lower alkylsulphonylamino is in the 3-position of the phenyl radical.

3. 7β-[D-2-Amino-2-(3-methylsulphonylamino-phenyl)-acetylamino]-3-methoxy-3-cephem-4-carboxylic acid, or a pharmaceutically acceptable salt thereof according to claim 1.

4. 7β[D-2-Amino-2-(3-methylsulphonylamino-phenyl)-acetylamino]-3-chloro-3-cephem-4-carboxylic acid, or a pharmaceutically acceptable salt thereof according to claim 1.

5. An antibacterial formulation for the treatment of animals infected with pathogenic bacteria comprising an antibacterially effective amount of a compound of the formula I according to claim 1 and a pharmaceutically acceptable carrier.

6. A method for the treatment of animals infected with pathogenic bacteria which comprises administering to said animals an antibacterial formulation according to claim 5.

* * * * *